United States Patent [19]

Phillipps et al.

[11] 4,192,871

[45] Mar. 11, 1980

[54] CHEMICAL COMPOUNDS

[75] Inventors: Gordon H. Phillipps, Wembley; Peter J. May, North Harrow; Barry E. Ayres, Ickenham, all of England

[73] Assignee: Glaxo Laboratories Limited, Greenford, England

[21] Appl. No.: 907,915

[22] Filed: May 22, 1978

Related U.S. Application Data

[63] Continuation of Ser. No. 752,513, Dec. 20, 1976, abandoned.

[30] Foreign Application Priority Data

Jan. 6, 1976 [GB] United Kingdom ............... 357/76

[51] Int. Cl.² .......................................... C07J 41/00

[52] U.S. Cl. .................................. 424/241; 424/238; 424/243; 260/239.5; 260/239.55 R; 260/397.3; 260/397.45; 260/397.5

[58] Field of Search ............. 260/239.5, 397.45, 397.5

[56] References Cited

U.S. PATENT DOCUMENTS 3,943,124  3/1976  Phillipps et al. ............... 260/239.55

*Primary Examiner*—Elbert L. Roberts
*Attorney, Agent, or Firm*—Bacon & Thomas

[57] ABSTRACT

Pregnanes and androstanes are described which essentially possess a 3α-hydroxy group, a 5α-hydrogen atom or a 4.5- or 5,6-double bond, a 17α-hydrogen atom and an 11β-aminoester group. Other optional substituents or double bonds may be present. The compounds have anaesthetic activity.

23 Claims, No Drawings

CHEMICAL COMPOUNDS

This is a continuation, of application Ser. No. 752,513, filed Dec. 20, 1976, now abandoned.

This invention relates to anaesthetic steroids.

Many steroids possessing anaesthetic activity are now known, these frequently being 3α-hydroxy 5α or Δ$^4$ compounds in the 17α-unsubstituted 20-oxo-pregnane and androstane series, the best compounds often having an 11-oxo group. These compounds are mostly insufficiently soluble in water, and it has been necessary to formulate them for administration in aqueous solutions of parenterally acceptable non-ionic surface active agents as for example described in British Patent Specification No. 1317184 with regard to the important anaesthetic 3α-hydroxy-5α-pregnane-11,20-dione. Anaesthetic steroids are also known which possess water-solubilising groups at various positions on the steroid nucleus for example at the 2β- or 3α-position or the 21-position in a pregnane or the 17-position in an androstane, but the introduction of the water-solubilising group has frequently resulted in a fall in activity or stability.

We have now found very interesting anaesthetic activity in a group of 3α-hydroxy 5α- or Δ$^4$ or Δ$^5$ pregnanes and androstanes and their 19-nor and D-homo analogues possessing an 11β-secondary or tertiary-aminoalkanoyloxy or aralkanoyloxy group, particularly in the water soluble salts of these compounds with acids.

This invention thus provides steroids of the pregnane and androstane series and their 19-nor analogues having a 3α-hydroxy group; a 5α-hydrogen atom or a 4,5- or 5,6-double bond; a 17α-hydrogen atom; and at the 11β-position a group of the formula $R^1COO-$ where $R^1$ is a $C_{1-6}$ alkyl group or a monocyclic aralkyl group having a $C_{1-6}$ alkyl portion, the alkyl group or alkyl portion being substituted by an amino group of the formula $-NR^aR^b$, in which $R^a$ and $R^b$ (which may be the same or different) are hydrogen atoms or substituted or unsubstituted alkyl, alkenyl, cycloalkyl, cycloalkenyl or phenalkyl groups (provided that at least one of $R^a$ and $R^b$ is other than hydrogen and that $R^a$ and $R^b$ together contain up to 14 carbon atoms) or in which $R^a$ and $R^b$ (together with the nitrogen atom) represent a saturated or ethylenically unsaturated non-aromatic monocyclic heterocyclic group having 3–10 ring members or a saturated or unsaturated bicyclic heterocyclic group having up to 10 ring carbon atoms (the ring containing the nitrogen atom being non-aromatic and either saturated or ethylenically unsaturated) which heterocyclic groups may be unsubstituted or substituted by for example one or more $C_{1-4}$ alkyl groups; and the 17aα-hydrogen D-homo analogues thereof; and the acid addition salts thereof.

In the tests we have carried out, the compounds of the invention have been shown generally to be good anaesthetics, usually giving instantaneous induction of anaesthesia when administered intravenously. The water soluble salts are particularly important in that they can be formulated in aqueous solution and in general comparison to known water soluble anaesthetic steroids they are superior as regards their potency and/or quality of anaesthesia and/or freedom from side effects such as thrombophlebitis. The aqueous solutions of the water soluble salts have also in general been found to be very stable. The compounds of the invention are of use for inducing anaesthesia which is to be maintained for example by an inhalation anaesthetic, such as ether, halothane, nitrous oxide or trichloroethylene. The compounds may also be capable of maintaining anaesthesia to a sufficient degree to enable surgical operations to be conducted without the aid of an inhalation anaesthetic, the anaesthesia being maintained if necessary by repeated or continuous administration. The compounds may have other desirable central nervous system depressant activities, for example they may be of use as sedatives.

The alkyl portion of the aminoalkyl group $R^1$ may be unbranched or branched, examples of suitable groups being methyl, ethyl, propyl, butyl and iso-butyl, methyl being preferred. Similar considerations apply to aminoaralkyl $R^1$ groups; in such groups, the aryl group may for example be phenyl, as for example in an aminobenzyl group.

The amino group $-NR^aR^b$ may be attached at any position along the alkyl portion of the group $R^1$. It is preferably attached to the α-position of the alkyl group in relation to the carbonyl group, as for example in the N-mono- or N,N-disubstituted aminomethyl, 1-aminoethyl, or 1-aminopropyl group. Substituted aminomethyl and 1-aminoethyl groups are preferred, particularly where the $-NR^aR^b$ group is as specified below. $R^a$ and $R^b$ may be substituted (e.g. by halogen) but they are preferably unsubstituted.

As indicated above, the group $-NR^aR^b$ must be a secondary or tertiary amino group and thus only one of $R^a$ and $R^b$ may be a hydrogen atom. As regards the $R^a$ and $R^b$ groups, they may for example be alkyl groups, which may be straight or branched, such as methyl, ethyl, propyl, butyl, iso-butyl, pentyl, sec-butyl, 2,2-dimethylpropyl, 2-methylbutyl, 1,3-dimethylbutyl, 1,5-dimethyl-pent-3-yl groups, or allyl groups. When $R^a$ or $R^b$ is a cycloalkyl or cycloalkenyl group, it may be for example a cyclopropyl, cyclopentyl, cyclohexyl, cyclohexenyl or an adamantyl group. When $R^a$ or $R^b$ is a phenalkyl group, it may for example be a benzyl or phenethyl group.

When the group $-NR^aR^b$ represents a group other than an heterocyclic amino group, $R^a$ and $R^b$ are preferably both unsubstituted alkyl groups or one of $R^a$ and $R^b$ is a hydrogen atom and the other is an unsubstituted alkyl group. Thus, in general, $R^a$ and $R^b$ together preferably contain 4–9, e.g. 4–7 carbon atoms. In particular, when $R^a$ and $R^b$ are the same they are preferably ethyl or propyl groups and when $R^a$ and $R^b$ are different, one of $R^a$ and $R^b$ preferably represents a methyl or ethyl group or a hydrogen atom. When one of $R^a$ or $R^b$ represents a methyl group, the other group preferably contains 4–6 carbon atoms and is especially a butyl, 2-methylbutyl or 1,3-dimethylbutyl group, and when one of $R^a$ or $R^b$ represents an ethyl group, the other group preferably contains 4–6 carbon atoms and is especially a butyl or 1,3-dimethylbutyl group. When one of $R^a$ and $R^b$ is hydrogen, the other group preferably contains 5–7 carbon atoms, the alkyl group desirably being branched, and is especially a 2-methylbutyl, 2,2-dimethylpropyl or 1,5-dimethylpent-3-yl group.

When one of $R^a$ and $R^b$ is an allyl, cyclohexyl, cyclopentyl, cyclopropyl, benzyl or phenethyl group, the other is preferably a hydrogen atom or a methyl or ethyl group.

When $-NR^aR^b$ represents a monocyclic heterocyclic group, the heterocyclic ring preferably has 4–9 ring members, as for example in azetidino, pyrrolidino, piperidino and hexamethylenimino groups. More preferably, these rings have 5–7 ring members. The rings may be substituted by one or two alkyl groups, e.g. methyl groups, such as in 2-, 3- or 4-methylpiperidino groups. The rings are preferably saturated, but they may be ethylenically unsaturated (but not aromatic) as for example in a tetrahydropyridino group.

When —NR$^a$R$^b$ represents a bicyclic heterocyclic group, the two rings may for example each have 5–7 ring members always provided that the total number of ring carbon atoms does not exceed 10. The ring which contains the nitrogen atom should not be aromatic, although it may be ethylenically unsaturated. An example of such a bicyclic group is a 3-azabicyclo(3,2,2)non-3-yl group. The bicyclic groups may be substituted by one or more alkyl, e.g. methyl groups.

When —NR$^a$R$^b$ is a heterocyclic group, it is preferably a monocyclic group.

The pregnanes, D-homo pregnanes and 19-nor pregnanes of the invention preferably have a 20-oxo group.

The androstanes and 19-nor androstanes of the invention may have for example a 17β-cyano, (C$_{2-6}$) alkoxycarbonyl, (C$_{2-6}$) alkylthiocarbonyl or disubstituted carbamoyl group. The D-homo androstanes may be similarly substituted at the 17aβ-position.

The terms "pregnane" and "androstane" include compounds having a methyl or ethyl group at the 13-position. Where a 13-ethyl group is present, the compound is conveniently in the 19-nor series.

Compounds having a 13-methyl group are generally preferred, as are compounds which have a 5-membered ring D.

The compounds of the invention are preferably of the pregnan-20-one or 17β-cyano-androstane series, the pregnan-20-ones being especially preferred.

The compounds of the invention may optionally be substituted at other positions of the steroid nucleus, for example at the 2,3β,6β, 16 and 21 positions. The compounds may also have a 1,2-double bond (when the 4-position is saturated) and/or a 8,9-double bond (when the 6-position is saturated). There is preferably only one such optional substituent in ring A and the 2-position should be unsubstituted when a 1,2-double bond is present.

Preferably, the compounds of the invention are of the formula:

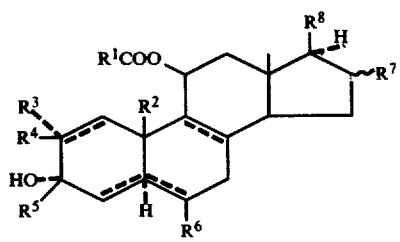

wherein:
R$^1$ is as defined above;
R$^2$ is a hydrogen atom or a methyl group;
R$^3$ is a hydrogen atom or optionally (when R$^4$ is a hydrogen atom) a C$_{1-3}$ alkyl group;
R$^4$ is a hydrogen atom or C$_{1-5}$ alkyl, C$_{1-5}$alkoxy (which may be substituted by a halogen atom, e.g. chlorine, or a phenyl group), C$_{2-5}$ alkanoyloxy, C$_{2-5}$ alkanoylthio, or thiocyanato group or a halogen atom;

R$^5$ is a hydrogen atom or a methyl group;
R$^6$ is a hydrogen atom or a methyl group;
R$^7$ represents two hydrogen atoms; a hydrogen atom in the β-position and a chlorine atom or methyl group in the 6β-position; a methyl group in the β-position and a hydrogen atom in the α-position; or a gem-dimethyl group; and
R$^8$ is a cyano group or a group —COR$^9$ where R$^9$ is a methyl group or a methyl group substituted by a fluorine atom, a C$_{1-4}$ alkoxy, hydroxy, methyl, chloromethyl, methoxymethyl, ethoxymethyl, C$_{2-5}$ alkanoyloxy, C$_{2-5}$ alkanoylthio, benzoyloxy, benzoylthio, or C$_{2-5}$ alkoxycarbonyloxy group; or where R$^9$ is a C$_{1-5}$ alkoxy, C$_{1-5}$ alkylthio or cyclopropyl group; or where R$^9$ is the group —NR$^x$R$^y$ where R$^x$ and R$^y$ (which may be the same or different) are methyl or ethyl groups; the broken lines indicate the optional presence of double bonds at the positions shown;
provided that R$^3$ and R$^4$ together represent a hydrogen atom when a 1,2-double bond is present; that the 2-position is saturated when a 4,5-double bond is present; and that the 6-position is saturated when a 8,9-double bond is present);
and the D-homo analogues carrying R$^8$ at the 17aβ-position and R$^7$ at the 17-position;
and the acid addition salts thereof.

When a 2α(R$^3$) substituent is present, it is preferably a methyl group.

Compounds having a 2β(R$^4$)-substituent are particularly important, examples of such substituents being a methyl, methoxy, ethoxy, propoxy, iso-propoxy, butoxy, or thiocyanato group or a fluorine, chlorine or bromine atom. When a 2β-substituent is present, there is preferably a hydrogen atom in the 5α-position.

R$^8$ is preferably a CH$_3$CO— or cyano group, the former being particularly preferred.

Compounds having a 5-membered ring D are generally preferred.

Compounds in the 5α-hydrogen 10-methyl series are generally preferred, as are compounds which are saturated within the tetracyclic steroid system and in which R$^3$, R$^5$, R$^6$ and R$^7$ are all hydrogen atoms and R$^8$ is an acetyl or cyano group. In such preferred compounds R$^4$ is preferably a hydrogen atom or a C$_{1-5}$ alkoxy group. A 2β-ethoxy group is an especially preferred alkoxy group.

As indicated above, the ability of the compounds of the invention to form water soluble acid addition salts is particularly important. The water solubility allows the salts to be formulated simply, and we have also surprisingly found that the salts are often superior in activity as compared to the parent free base.

Examples of suitable salts are hydrochlorides, hydrobromides, phosphates, sulphates, p-toluenesulphonates, methanesulphonates, citrates, tartrates, acetates, ascorbates, lactates, maleates, succinates, tricarballylates, glutarates, aconitates, citraconates and glutaconates. The citrates and tricarballylates are particularly preferred for use as anaesthetics.

When these salts are used as anaesthetics they should be physiologically acceptable at the dosage at which they are administered. Other salts may, however, be of use in for example isolation of the product from a synthetic reaction.

Compounds which are preferred on account of the activity shown in our tests are:

1. 11β-N,N-dipropylaminoacetoxy-3α-hydroxy-5α-pregnan-20-one and its phosphate, citrate, tricarballylate, hydrochloride, hemisulphate, tartrate, lactate and glutarate salts;
2. 11β-piperidinoacetoxy-3α-hydroxy-5α-pregnan-20-one and its citrate and hydrochloride salts;
3. 11β-(3-methylpiperidinoacetoxy)-3α-hydroxy-5α-pregnan-20-one and its citrate salt;
4. 11β-(4-methylpiperidinoacetoxy)-3α-hydroxy-5α-pregnan-20-one and its citrate salt;
5. 11β-(2-methylpiperidinoacetoxy)-3α-hydroxy-5α-pregnan-20-one and its citrate salt;
6. 11β-N,N-diethylaminoacetoxy-2β-ethoxy-3α-hydroxy-5α-pregnan-20-one and its citrate salt.
7. 11β-hexamethyleniminoacetoxy-3α-hydroxy-5α-pregnan-20-one and its citrate salt;
8. 2β-ethoxy-11β-N,N-dipropylaminoacetoxy-3α-hydroxy-5α-pregnan-20-one and its citrate and tricarballylate salts;
9. 2β-methyl-11β-N,N-dipropylaminoacetoxy-3α-hydroxy-5α-pregnan-20-one and its citrate salt;
10. 11β-N-methyl-N-butylaminoacetoxy-3α-hydroxy-5α-pregnan-20-one and its citrate salt;
11. 2β-ethoxy-11β-N-methyl-N-butylaminoacetoxy-3α-hydroxy-5α-pregnan-20-one and its citrate salt;
12. 11β-N-ethyl-N-butylaminoacetoxy-3α-hydroxy-5α-pregnan-20-one and its citrate, hydrochloride and tricarballylate salts;
13. 2β-propoxy-11β-N,N-diethylaminoacetoxy-3α-hydroxy-5α-pregnan-20-one and its citrate salt;
14. 3α-hydroxy-11β-2'-methylbutylaminoacetoxy-5α-pregnan-20-one and its citrate salt;
15. 3α-hydroxy-3β-methyl-11β-piperidinoacetoxy-5α-pregnan-20-one and its citrate salt;
16. 3α-hydroxy-11β-N-methyl-N-2'-methylbutylaminoacetoxy-5α-pregnan-20-one and its citrate salt;
17. 17β-cyano-3α-hydroxy-11β-N,N-dipropylaminoacetoxy-5α-androstane and its citrate salt;
18. 3α-hydroxy-11β-N-methyl-N-1',3'-dimethylbutylaminoacetoxy-5α-pregnan-20-one and its citrate salt;
19. 3α-hydroxy-11β-N-methyl-N-[(2R)-1',3'-dimethylbutyl)] aminoacetoxy-5α-pregnan-20-one and its citrate salt;
20. 3α-hydroxy-11β-N-methyl-N-[(2S)-1',3'-dimethylbutyl] aminoacetoxy-5α-pregnan-20-one and its citrate salt;
21. 11β-N,N-diethylaminoacetoxy-3α-hydroxy-5α-pregnan-20-one and its citrate salt;
22. 11β-N,N-di(but-2-yl)aminoacetoxy-3α-hydroxy-5α-pregnan-20-one and its citrate salt;
23. 11β-N-1',3'-dimethylbutyl-N-ethylaminoacetoxy-3α-hydroxy-5α-pregnan-20-one and its citrate salt;
24. 11β-N-2',2'-dimethylpropylaminoacetoxy-3α-hydroxy-5α-pregnan-20-one and its citrate salt;
25. 11β-N,N-diethylaminoacetoxy-3α-hydroxy-2β-methyl-5α-pregnan-20-one and its citrate salt;
26. 11β-N-ethyl-N-butylaminoacetoxy-3α-hydroxy-2β-methyl-5α-pregnan-20-one and its citrate salt;
27. 3α-hydroxy-2β-methyl-11β-(4'-methylpiperidinoacetoxy)-5α-pregnan-20-one and its citrate salt;
28. 2β-ethoxy-3α-hydroxy-11β-N-3'-methylbutylaminoacetoxy-5α-pregnan-20-one and its citrate salt;
29. 2β-ethoxy-3α-hydroxy-11β-N-1',3'-dimethylbutylaminoacetoxy-5α-pregnan-20-one and its citrate salt;
30. 11β-N,N-diethylaminoacetoxy-3α-hydroxy-2β-isopropoxy-5α-pregnan-20-one and its citrate salt;
31. 2β-bromo-3α-hydroxy-11β-N-butyl-N-methylaminoacetoxy-5α-pregnan-20-one and its citrate salt; and
32. 11β-N-butyl-N-methylaminoacetoxy-17β-cyano-3α-hydroxy-5α-androstane and its citrate salt. Of the above-mentioned compounds, compound Nos. 1–8, 10–15, 17–21, 23, 24 and 29 are particularly preferred on account of the activity shown in our tests. Compounds Nos. 6, 10 and 12 are especially preferred.

PHARMACEUTICAL FORMULATIONS

The compounds of the invention may be formulated as convenient, following generally known pharmaceutical practices, (including both human and veterinary medical practices), with the aid of one or more pharmaceutical carriers or excipients. For anaesthetic purposes, the steroids will be given by injection and thus one aspect of this invention comprises a composition for parenteral administration comprising an anaesthetic compound in accordance with the invention in a parenterally acceptable vehicle.

When the compounds are sufficiently soluble in water (e.g. the salts) they may be presented in aqueous injecton vehicles. The preparation of suitable solutions by bringing the free bases into solution in aqueous acid is described below. For induction anaesthesia, these solutions will usually contain 0.25–4.0% (conveniently 0.5–2%) w/v of the active compound, but stronger solutions may be prepared with the more soluble salts. If desired, the free base and the acid required for salt formation may be packed separately in two-pack form for formulation as and when needed. Alternatively the steroid salt and the aqueous injection vehicle may be packed separately in two-pack form.

Although the compounds of the invention are preferably formulated as simple aqueous solutions of their salts, the free bases may also be formulated in an aqueous solution of a parenterally acceptable non-ionic surface active agent in the same way (and using the same proportions of materials) as described in our British Patent Specification 1317184 for 3α-hydroxy-5α-pregnane-11,20-dione. The simple aqueous solutions have the advantage for example of avoiding anaphylactoid responses in surfactant-sensitive species.

The anaesthetic solutions according to the invention are generally administered by intravenous injection although in certain cases (e.g. with children or animals) intramuscular injection might be preferred. The simple aqueous solutions of the salts may also be administered subcutaneously.

As is usual in the case of anaesthetics, the quantity of steroid used to induce anaesthesia depends upon the weight of the individual to be anaesthetised. For intravenous administration in the average man a dose of from 0.1 to 8.0 mg/kg will in general be found to be satisfactory to induce anaesthesia, the preferred dose being within the range of from 0.2 to 4.0 mg/kg. The dose will naturally vary to some extent, dependent upon the physical condition of the patient and the degree and period of anaesthesia required.

If it is desired to maintain prolonged anaesthesia, repeated doses of the above solutions may be used, such repeated doses being generally either of the same order or lower than the original dose. Alternatively continuous administration may be undertaken using solutions containing 0.025–0.4% (preferably 0.05–0.2) w/v of the active compound at for example a rate of 0.0125–0.2 (e.g. 0.025–0.1) mg/kg/min. Continuous administration can also be used to produce sedation for prolonged periods.

Where the anaesthetic solutions are administered intramuscularly or subcutaneously, higher doses are generally necessary.

COMPOUND PREPARATION

The compounds of the invention may be prepared by a number of different methods, using generally known techniques. Suitable methods are described below.

(a) Reaction of an amine $HNR^aR^b$ with a corresponding 11β-alkanoyloxy or -aralkanoyloxy compound having a readily displaceable substituent in the alkyl portion. This reaction is probably the most convenient method of preparing the compounds of the invention. The displaceable substituent may for example be a hydrocarbyl sulphonyloxy group (e.g. tosyloxy or mesyloxy) but is preferably an iodine, chlorine or bromine atom. The reaction is generally carried out at a temperature of 0°–100° C., e.g. 15°–30° C., in a suitable solvent, which may be the amine itself or an inert solvent such as acetonitrile, dimethylformamide, acetone, ethanol, diethyl ether, ethyl acetate, tetrahydrofuran, toluene, methylene chloride or ethylene dichloride. This reaction is conveniently carried out in the presence of an acid binding agent, e.g. an excess of the amine.

If, under the reaction conditions employed, the 20-oxo group reacts with the amine, the 20-oxo group can readily be regenerated, for example by acidic hydrolysis.

Where an 11β-chloroacetate is used as starting material, the reaction is conveniently effected in the presence of iodide ions, e.g. sodium iodide.

The reaction conditions just described are particularly suitable for the preparation of the amino acetates of the invention. Where the alkyl chain in the group $R^1$ is longer, as for example in the aminopropionates, forcing conditions are often required, for example the use of temperatures up to 130° C. using the amine or dioxan as the solvent.

As will be evident, the above process may not be suitable for the direct preparation of compounds which contain base-sensitive groupings, e.g. halo or thiocyanato substituents, at the 2β, 16α or 21-positions. Also, protected 3α-hydroxy or 20-oxo compounds can be used in this reaction, the protecting group being subsequently removed.

The 11β-substituted esters used as starting materials in this reaction are themselves new compounds and again may be prepared by a variety of known methods. The 11β-halo alkanoyloxy and aralkanoyloxy compounds also have shown anaesthetic activity, in particular those compounds corresponding to the 11β-aminoesters of formula I. The iodo compounds may for example be prepared from the corresponding chloro compounds by reaction with an alkali metal iodide (e.g. sodium iodide) in a suitable solvent, e.g. acetone. The chloro compounds are conveniently prepared by esterification of the corresponding 11β-hydroxy compound with a chloro carboxylic acid or a reactive derivative thereof (such as an acid halide, e.g. chloride, or preferably an acid anhydride). This reaction is desirably carried out using a basic catalyst such as 4-dimethylaminopyridine. The reaction may be performed in a suitable solvent (e.g. an ether such as dioxan) at a temperature of 20°–100° C. The 11β-hydroxy compounds required as starting materials in this reaction may themselves be prepared by reducing the readily obtainable 11-oxo compounds, e.g. with sodium borohydride, after suitably protecting a 20-oxo group when present by for example ketal formation.

The 11β-substituted esters used as starting materials may also be prepared by reduction of the corresponding 3-oxo 5α or 66⁵-compound, deesterification of a corresponding 3-ester or deketalisation of a corresponding 20-ketal. In such preparations, generally the same methods may be used as described below with regard to the preparation of the compounds of the invention.

(b) Deprotection of a corresponding compound having a protected 3α-hydroxy group. This method is often a convenient last stage in the preparation of the compounds of the invention in that the 3α-hydroxy group is often either deliberately protected or is itself esterified during the introduction of the ester group at the 11β1-position or is formed in the esterified state by inversion from a 3β-hydroxy compound (for example by treating the 3β-alcohol with diethyl azodicarboxylate in the presence of an acid such as formic or benzoic acid and a phosphine such as triphenylphosphine). The group present at the 3α-position in the starting materials in this reaction may thus be the same ester group as is present at the 11β-position of the compounds of the invention, i.e. a group of the formula $R^1COO$. Such esters may be hydrolysed to give the desired 3α-hydroxy compounds under mild acid or basic conditions. Weakly basic conditions are generally most convenient (using for example an alkali metal bicarbonate in aqueous methanol at any suitable temperature up to reflux). Dilute mineral acids (e.g. perchloric acid in aqueous methanol) may also be used. Strong bases (e.g. alkali metal hydroxides) may be used if the reaction is carried out briefly.

Alternatively, the starting material in this reaction may be a protected 3α-hydroxy compound such as a 3α-ether (e.g. 3α-tetrahydropyranyl ether) or a 3α-nitrooxy compound. Such ether protecting groups may be removed by treatment with an aqueous acid, and such ester groups may be removed by reduction, for example using zinc and acetic acid.

(c) Ring A-saturated 2β-unsubstituted 5α-steroids of the invention may be prepared from appropriate 3-oxo compounds by stereospecific reduction, e.g. by the method of Browne and Kirk (J. Chem. Soc. C, 1969, 1653) or by the method of our British Patent Specification No. 1409239. The latter method preferably uses a pre-formed iridium catalyst reduction system. For example, a reduction system may be prepared from an iridium acid or salt (e.g. chloroiridic acid), trivalent phosphorus compound such as a phosphorus acid ester (e.g. trimethyl phosphite), water and an organic reaction medium (e.g. an alcohol such as isopropanol). The reduction system is then neutralised (e.g. to a pH of 6 to 8.5) with an organic base such as a secondary or tertiary amine (e.g. triethylamine) and reacted with the steroid. When the catalyst system is preformed, by heating at reflux, e.g. for 16 to 72 hours, the reduction can be accomplished for example in 2–3 hours at reflux; longer times may be necessary at room temperature.

(d) Deketalisation of a corresponding 20-ketal.

It is frequently necessary or desirable to protect a 20-oxo group during the preparation of the pregnanes of the invention, for example in the form of a ketal. The 20-oxo group may then be regenerated as the final step in the preparation. The ketal is preferably the corresponding 20,20-ethylenedioxy compound, and the 20-oxo group may be regenerated for example by hydrolysis in the presence of an acid (e.g. hydrochloric or acetic acid), or by exchange reaction with a ketone e.g. acetone in the presence of an acid catalyst, e.g. p-toluenesulphonic acid, at a temperature of 0°–100° C.

(e) Opening of a corresponding Ring A—saturated $2\alpha,3\alpha$-epoxide.

This reaction may be used to prepare compounds in accordance with the invention which possess a $2\beta$-substituent, and it is the preferred way of making the $2\beta$-halo, haloalkoxy and thiocyanato compounds. The general method of preparing $2\beta$-compounds by this route is described in our British Patent Specification 1376892. Thus in general the reaction comprises treating the corresponding $2\alpha,3\alpha$-epoxide with a compound $HR^4$ under acidic conditons (if necessary in the presence of an added acid catalyst, e.g. sulphuric acid or boron trifluoride). Examples of $HR^4$ compounds are alcohols, carboxylic acids, thiocarboxylic acids, thiocyanic acid and hydrogen halides. The reaction is preferably carried out under anhydrous conditions in a suitable solvent (e.g. a hydrocarbon or an ether) at any suitable temperature up to reflux. $2\beta$-Halo and thiocyanato compounds may also be prepared in aqueous media.

The starting materials required for this reaction may for example be prepared by the method of reaction (a) above using a $2\alpha,3\alpha$-epoxide starting material, which latter compound may be made by 11-halo esterification and epoxidation of the corresponding $11\beta$-hydroxy $\Delta^2$-compound.

(f) Conversion of a corresponding unsubstituted or monosubstituted $11\beta$-amino ester into a mono- or disubstituted $11\beta$-amino ester.

This reaction may be performed by reacting a compound in which one or both of $R^a$ and $R^b$ is hydrogen with a compound of the formula $R^aX$ where X is a readily displaceable group such as halide (e.g. iodide) or a hydrocarbylsulphonyloxy group, e.g. a toluene-p-sulphonyloxy group. The reaction may be carried out in a polar solvent (such as dimethylformamide, acetone or ethanol) or using an excess of the compound $R^aX$, e.g. methyl iodide.

The N-unsubstituted starting material may be prepared by the same general method as described for reaction (a) above, e.g. by reacting a corresponding $11\beta$-halo ester with ammonia.

When an N-unsubstituted starting material is used, this reaction can produce either N-mono or N,N-di-substituted compounds of the invention, and when a N-mono-substituted starting material is used, the reaction can produce N,N-disubstituted compounds of the invention in which $R^a$ and $R^b$ are either the same or different groups.

Alternatively, this process may be performed by reacting the corresponding unsubstituted or N-monosubstituted $11\beta$-amino ester (or a 20-ketal thereof) with an appropriate mono- or di-carbonyl compound in the presence of a reducing agent. For example, with unsubstituted $11\beta$-amino esters the use of simple aldehydes or ketones (such as formaldehyde, acetaldehyde or acetone) can provide the $11\beta$-N-monomethyl or -dimethyl or N-mono-ethyl or -diethyl or N-isopropyl or -diisopropyl amino esters (depending partly on the proportion of aldehyde or ketone used), whereas a dialdehyde or diketone gives a $11\beta$-cyclic amino ester (e.g. glutardialdehyde may be used to form a piperidino group). When an N-mono-substituted $11\beta$-amino ester starting material is used, a mono-carbonyl compound should be used. The reducing agents which may be used are those generally known for the reduction of imines, examples being formic acid (e.g. at any suitable temperature up to 100°–120° C., using an excess of formic acid and using the aldehyde or ketone as the reaction solvent, in the presence or absence of water), an alkali metal borohydride or cyanoborohydride (e.g. sodium borohydride or cyanoborohydride, using an alcohol such as ethanol as solvent, suitably at room temperature preferably at pH 4–6), iron pentacarbonyl or an alkali metal hydrogen iron carbonylate (e.g. $Fe(CO)_5$ or $MHFe(CO)_4$ where M is sodium or potassium, at any suitable temperature up to reflux using an ether such as tetrahydrofuran or an alcohol or aqueous alcohol as solvent), hydrogen in the presence of a metal catalyst (e.g. palladium, using an alcohol or an ester such as ethyl acetate as reaction solvent, conveniently at room temperature), or aluminium amalgam in the presence of water (conveniently at room temperature, and in the presence of an ether solvent such as tetrahydrofuran). If desired the intermediate imino compound may be isolated.

(g) Conversion of a N,N-di-substituted $11\beta$-amino ester into a corresponding N-mono-substituted compound.

Compounds of the invention in which one of $R^a$ and $R^b$ is hydrogen can be prepared from corresponding compounds in which both $R^a$ and $R^b$ are groups other than hydrogen by replacement of one of the groups by a hydrogen atom, e.g. by dealkylation or de-aralkylation (e.g. de-benzylation) using for example catalytic hydrogenolysis.

(h) Reduction of the corresponding $\Delta^{16}$ compound.

This reaction may be performed for example by hydrogenating the starting material in the presence of a hydrogenation catalyst (e.g. a palladium catalyst) in a suitable solvent (e.g. an alcohol, ether or ester). The reaction is preferably effected in the presence of a tertiary base, e.g. triethylamine, except where an easily displaceable substituent (e.g. bromo) is at the $2\beta$-position.

(i) Reaction of an amine with a corresponding $11\beta$-alk-2-enoyloxy compound.

This reaction provides a convenient method of preparing 3'-aminopropionates and 3'-aminobutyrates. Suitable starting materials are compounds in accordance with the invention in which $R^1$ is $CH_2=CH-$ or $CH_3CH=CH-$, and these compounds may be reacted with an amine of the formula $HNR^aR^b$ to give the desired final product.

If under the reaction conditions employed, the 20-oxo group reacts with the amine, the 20-oxo group can readily be regenerated, for example by acid hydrolysis.

The starting materials necessary for this reaction may for example be prepared by reacting the corresponding $11\beta$-hydroxy compound with crotonic or acrylic anhydride in the presence of a base.

(j) Inversion of the corresponding $3\beta$-hydroxy compounds.

This preparative method is suitable for the preparation of compounds which are unsubstituted at the $3\beta$-position and do not possess a 5,6-double bond. The starting material may be a corresponding compound possessing a readily displaceable $3\beta$-group such as a hydrocarbylsulphonyloxy (e.g. p-toluenesulphonyloxy)

group, and the 3β-group may be displaced by hydrolysis (e.g. in acid conditions) to give the desired 3α-hydroxy compounds. Methods for preparing $\Delta^4$ compounds by this route are described in our British Patent Specification 1372175.

(k) Hydrochlorination of the corresponding $\Delta^{16}$-compound.

This reaction produces 16α-chloro substituted compounds, and may be performed by reacting the $\Delta^{16}$-compound with hydrogen chloride in an anhydrous solvent (e.g. an ether) at a temperature of for example 15°–40° C., as generally described in our British Patent Specification 1380248.

(l) Reaction of the corresponding $\Delta^{16}$- or 16-methyl-$\Delta^{16}$-compound with a metal methyl derivative.

This reaction can be used to give the 16α-methyl or 16-gem-dimethyl compounds, and may be performed by reacting the appropriate $\Delta^{16}$-compound with a metal methyl derivative such as lithium dimethyl cuprate in an ether solvent, again as generally described in our British Pat. Specification No. 1380248.

(m) Dehydration of a corresponding 17β-carbamoyl-11β-(N,N-disubstituted)amino ester or the oxime of a corresponding 17β-formyl-11β-(N,N-disubstituted)amino ester compound.

17β-Cyano compounds may be prepared by dehydrating the appropriate oxime for example with acetic anhydride at reflux. The 3α-hydroxy group will generally be esterified in this reaction and has to be regenerated by de-esterification. Alternatively, the corresponding 17β-(unsubstituted carbamoyl) compound can be dehydrated, e.g. by using polyphosphate ethyl ester, as described in our British Patent Specification 1380246.

(n) Esterification of a corresponding 17β-carboxylic or thiocarboxylic acid.

17β-Alkoxycarbonyl or alkylthiocarbonyl compounds may be prepared by reacting the corresponding 17β-carboxylic or thiocarboxylic acid or a reactive derivative thereof (e.g. an acid halide or anhydride) with the appropriate alcohol, thiol or alkyl halide. This reaction is preferably carried out in the presence of an acid binding agent (e.g. a tertiary base such as pyridine) at temperatures of −20° C. to 110° C., as is described for example in our British Patent Specification 1380246 and our British Pat. No. 1436549.

(o) Reaction of the corresponding 17β-carboxylic acid (or a derivative thereof) with an amine.

17β-(Substituted carbamoyl) compounds may be prepared by reacting the corresponding 17β-carboxylic acid or a reactive derivative thereof (e.g. an acid halide or ester) with an amine $HNR^xR^y$, where $R^x$ and $R^y$ are as defined above. This reaction is again preferably carried out in the presence of an acid binding agent, as is described generally in our British Patent Specification 1380246.

(p) Acyloxylation of a corresponding 21-unsubstituted compound.

21-Alkanoyloxy and benzoyloxy compounds may be prepared by treating the corresponding 21-unsubstituted compound (in which the 3α-hydroxy group is optionally protected) with the appropriate lead tetraacylate e.g. lead tetraacetate, preferably in the presence of a Lewis acid (e.g. boron trifluoride) in a hydrocarbon/alcohol solvent. This reaction is generally described in our British Pat. Specification No. 1317185.

(q) Displacement of a 21-iodine atom by fluoride.

21-Fluorides may be prepared from the corresponding 21-iodo compounds by treatment with a source of fluoride ions (e.g. an alkali metal or silver fluoride), as described generally in our British Pat. No. 1430932

(r) Deacylation of a corresponding 21-acyloxy compound.

21-Hydroxy compounds may be prepared by hydrolysing a corresponding 21-acyloxy compound (e.g. a 21-acetoxy compound) under basic conditions, as generally described in our British Pat. Specification No. 1377608.

(s) Etherification of a corresponding compound having a displaceable 21-substituent.

21-Alkoxy compounds may be prepared by etherifying a corresponding compound having a substituent at the 21-position (e.g. a 21-hydroxy or 21-halo, e.g. 21-bromo, compound), these methods being again generally described in our British Patent Specification 1377608. The 3α-hydroxy group is desirably protected in these reactions.

(t) Selective acylthiolation or acyloxylation of a corresponding 21-substituted compound.

21-Alkanoylthio, alkanoyloxy, benzoylthio and benzoyloxy compounds may be prepared by reacting a corresponding compound having a readily displaceable substituent at the 21-position (e.g. a bromine, chlorine or iodine atom or a hydrocarbyl sulphonyloxy group) with a salt of the appropriate carboxylic or thiol carboxylic acid. This reaction is generally described in our British Pat. No. 1432135 and our British Patent Specification 1317185.

(u) Selective acylation of the corresponding 21-alcohol or thiol.

21-Alkanoylthio, alkanoyloxy, benzoylthio and benzoyloxy compounds may also be prepared by acylating the corresponding 21-thiol or alcohol, again as described generally in our British Patent Specification No. 1432135 and our British Patent Specification 1317185. 21-Carbonate esters may similarly be prepared by using for example the appropriate alkylchloroformate.

(v) Dehydrohalogenation of a corresponding 2β-halo compound.

$\Delta^1$-Compounds may be prepared by dehydrohalogenating a corresponding 2β-halo compound (preferably a 2β-bromo compound) using for example a nitrogen-containing Lewis base, e.g. dimethylformamide or dimethylacetamide. The starting material may have a protected 3α-hydroxy group, and the reaction is advantageously carried out in the presence of an alkali metal or alkaline earth metal carbonate or halide (e.g. a mixture of calcium carbonate and lithium bromide) at a temperature of 80°–170° C. This reaction is described generally in our British Patent Specification 1380248.

(w) Salt formation.

Compounds of the invention are desirably used in the form of a salt, and thus salt formation by reaction of the base with an acid is particularly important.

A generally convenient method of forming the salts is to mix appropriate quantities of the free base and the acid in a mixture of water and a solvent for the base (e.g. an alcohol such as ethanol), removing the solvent (e.g. by evaporation) and then if desired dissolving the residue in the water. In most cases it is possible to form an aqueous solution of the salt by simply mixing the free base with an aqueous acid.

In these preparations, the base and the acid are not necessarily used in equivalent quantities; in some cases for example it is found that an excess of the base may be used, implying that the free base is dissolved to some extent in the solution of the salt. When the acid is a weak acid, an excess of the acid is sometimes desirable.

The methods indicated above for preparing the compounds of the invention can be used as the last main step in a preparative sequence. The same general methods can be used for the introduction of the desired groups or unsaturation at an intermediate stage in the stepwise formation of the required compound, and it will be appreciated that these general methods can be combined in many different ways in such multi-stage processes, as will be apparent from the Examples below. Thus for example the desired 11β-ester group may be formed either before or after the reduction of a 3-oxo group or 16,17-double bond, and either before or after the introduction of an optional substituent at the 2β,16,17β or 21-positions or the formation of a double bond at the 1,2-position. The sequence of the reactions in multi-stage processes should of course be chosen so that the reaction conditions used do not effect groups in the molecule which are desired in the final product.

Other structural features which may be present in the compounds of the invention may be introduced by the following methods.

Methods for introducing substituents at the 2α,3β, and 16β positions are described in our British Pat. Specification No. 1380248.

$\Delta^4$-Steroids may be obtained by the methods described in our British Pat. Specification No. 1372175.

Compounds having a double bond between the 8- and 9-positions may be prepared for example by the method described in our British Pat. Specification No. 1380248. These compounds may also be prepared by dehydration of the corresponding 9α-hydroxy compound, for example using thionyl chloride in pyridine.

Compounds having an alkyl or substituted alkyl group at the 21-position or a cyclopropyl group at the 20-position may be prepared by the methods generally described in our British Pat. No. 1436324.

Compounds having a 6β-methyl group may be prepared by hydrogenating a corresponding 6-methyl 3-oxo 4,6-diene, followed by reduction of the 6β-methyl-3-oxo-5α-compound formed, e.g. using chloroiridic acid as described above.

The D-homo and $\Delta^5$ compounds may be prepared by choice of starting materials having a D-homo or $\Delta^5$ structure.

The following examples illustrate the invention.
Temperatures are in °C.

Melting-points were determined on a Kofler block and are uncorrected. Optical rotations were determined at room temperature on solutions in chloroform (ca.1% w/v) unless otherwise stated.

Preparative TLC (thin layer chromatography) and column chromatography were carried out over silica.

Chloroiridic acid reagent was prepared by refluxing a mixture of chloroiridic acid (50 mg), isopropanol (94 ml), water (6 ml) and trimethyl phosphite (8 ml) for 24 hours and adjusted to pH 7 by the addition of triethylamine immediately prior to use.

'Petrol' refers to petroleum ether, b.p. 60°-80°.

Methylene chloride (dichloromethane) was redistilled and dried.

Solutions were dried either azeotropically or by use of magnesium or sodium sulphate.

In the Tables which follow MC=methylene chloride; DC=1,2-dichloroethane; EA=ethyl acetate; PE=petroleum ether; M=methanol; W=water; Ac-=acetone; ET=ethanol; Ch=chloroform; DE=diethyl ether; D=dioxan.

EXAMPLE 1

3α-Hydroxy-11β-dipropylaminoacetoxy-5α-pregnan-20-one

A mixture of 3α,11β-bis-N,N-dipropylaminoacetoxy-5α-pregnan-20-one (300 mg) and sodium bicarbonate (300 mg) in methanol (20 ml) containing water (2 ml) was refluxed for a total of 27 hours during a period of 5 days. The mixture was diluted with water and the solid material which precipitated was collected by filtration and recrystallized from ether-petroleum ether to yield title compound, m.p. 116.5°-118°, $[\alpha]_D+96.5°$, (110 mg).

EXAMPLE 2

11β-Dipropylaminoacetoxy-3α-hydroxy-5α-pregnan-20-one

11β-Dipropylaminoacetoxy-5α-pregnane-3,20-dione (300 mg) was added to a solution of chloroiridic acid reagent (10 ml) containing triethylamine (1.1 ml). The mixture was boiled for about 20 minutes, cooled and diluted with sodium bicarbonate solution and the precipitated solid collected by filtration to afford title compound, m.p. 107°-115°, $[\alpha]_D+91.3°$ (230 mg).

EXAMPLE 3

3α-Hydroxy-11β-dipropylaminoacetoxy-5α-pregnan-20-one

Toluene-4-sulphonic acid (120 mg) was added to a solution of 20,20-ethylenedioxy-11β-dipropylaminoacetoxy-5α-pregnan-3α-ol (260 mg) in acetone (20 ml). The mixture was kept at room temperature until reaction was judged complete (TLC), when sodium bicarbonate solution was added and the precipitated material collected by filtration. Crystallization from ether-petroleum ether afforded title compound, m.p. 120°-122°, $[\alpha]_D+92°$.

EXAMPLE 4–73

Preparation of 11β-aminoacetates

Table 1 (a) summarises the preparation of 11β-aminoacetates by the following method.

The appropriate 3α-hydroxy-11β-iodoacetoxy-5α-pregnan-20-one in the solvent indicated was treated with the appropriate amine for the specified time and evaporated in vacuo.

Table 1(b) summarises the preparation of 11β-aminoacetates by the following method:

The appropriate 3α-hydroxy-11β-chloroacetoxy-5α-pregnan-20-one and sodium iodide in the solvent indicated were treated with the appropriate amine for the specified time and evaporated to low bulk.

The residue from either of the above two methods was then worked-up by one of the following methods:

A. The residue was triturated with water and the precipitated material was collected by filtration, washed thoroughly with water and dried.

B. The residue was partitioned between water and ethyl acetate, and the organic extract washed, dried and evaporated.

C. The residue was partitioned between ethyl acetate and sodium bicarbonate solution, washed, dried and evaporated.

D. The reaction mixture, prior to evaporation, was diluted with chloroform, washed thoroughly with water and evaporated in vacuo.

E. The residue was partitioned between dilute hydrochloric acid and ethyl acetate, the aqueous layer basified with sodium bicarbonate solution and re-extracted into ethyl acetate, which was then washed, dried and evaporated in vacuo.

F. The reaction mixture, prior to evaporation, was partitioned between chloroform and water, and the organic layer washed, dried and evaporated.

G. The reaction mixture, prior to evaporation, was diluted with water, extracted with ethyl acetate and evaporated.

H. The reaction mixture, prior to evaporation, was diluted with water, extracted with ethyl acetate and the combined extracts were extracted with hydrochloric acid. The acidic extract was basified with sodium hydroxide, re-extracted with ethyl acetate and evaporated.

The material obtained by one of these procedures was purified by preparative TLC and/or crystallisation.

The compounds prepared were of the general formula:

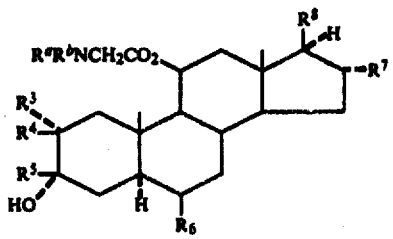

$R^8$ was —COCH$_3$ in Examples 4–13, 15–66 and 68–73; —COOCH$_3$ in Example 14; and —COCH$_2$OCH$_3$ in Example 67.

$R^4$ was H in Examples 4–8, 14–41, 44–54, 56–58, 66, 67 and 71–73; —OC$_2$H$_5$ in Examples 9,10,43 and 59–61; —OC$_3$H$_7$ in Examples 11 and 42; —OCH$_3$ in Examples 12 and 13; —OCH(CH$_3$)$_2$ in Example 62; —OC$_4$H$_9$ in Examples 63 and 64; —OCOCH$_3$ in Example 65; and —CH$_3$ in Examples 55 and 68–70.

$R^5$ was H in Examples 4–20 and 25–73 and —CH$_3$ in Examples 21–24.

$R^3$ was H in Examples 4–70 and 72 and 73 and —CH$_3$ in Example 71.

$R^6$ was H in Examples 4–65 and 67–73 and —CH$_3$ in Example 66.

$R^7$ was H in Examples 4–71 and —CH$_3$ in Examples 72 and 73.

4,192,871

TABLE 1(a)

| Ex. | —NR$^a$R$^b$ | Iodo-acetate (g) | Amine (ml) | Solvent | Vol (ml) | Reaction time (hrs) | TLC system | Crystallisation solvent | Yield (g) | m.p. (°C.) | [α]$_D$ c g/100 ml | Method of work-up |
|---|---|---|---|---|---|---|---|---|---|---|---|---|
| 4 | —N(Me)(Et) | 1.5 | 3 | DC | 60 | 21 | — | EA-PE | 1.08 | 141.5-143 | +105° | A |
| 5 | —N(Me)(Pr) | 1.5 | 3 | MC | 60 | 20 | — | M-W | 1.116 | 101-102 | +97° | D |
| 6 | —N(CH$_2$CH=CH$_2$)$_2$ | 1.5 | 3 | DC | 60 | 144 | — | PE | 1.203 | 134-136 | +93.5° | A |
| 7 | —N(C$_5$H$_{11}$)$_2$ | 1.5 | 3 | DC | 60 | 96 | *EA | PE | 0.751 | 98.5-99.5 | +87.5° | B |
| 8 | —N(Me)(CH$_2$Ph) | 1.5 | 3 | DC | 59 | 24 | — | EA-PE | 1.19 | 93.5-95 | +90.2° | A |
| 9 | —NPr$_2$ | 0.478 | 2 | MC | 20 | 24 | EA | EA-PE | 0.320 | 138-141 | +91.2° | D |
| 10 | —N(Me)(Bu) | 0.990 | 4 | MC | 30 | 24 | Ac-PE | — | 0.607 | — | +95° | C |
| 11 | —NEt$_2$ | 1.25 | 4 | MC | 25 | 3.5 | EA Ac-PE | DE-PE | 0.282 | 123-132 | +96° | C |
| 12 | —NEt$_2$ | 0.472 | 1 | MC | 10 | 3 | (1) Ac-PE Ch-EA-Ac | DE-PE | 0.126 | 129-133 | +104.7°(0.5) | C |
| 13 | piperidine | 0.466 | 1 | MC | 10 | 3 | Ac-PE EA-Ch-Ac | DE-PE | 0.210 | 129-133 | +99.2° | C |
| 14 | piperidine | 0.456 | 1 | MC | 10 | 2 | — | M-W | 0.383 | 170-175 | +62.0° | A |
| 15 | —N(Me)(CH$_2$CH$_2$Ph) | 1.5 | 3 | DC | 50 | 72 | — | EA-PE | 1.06 | 79-80 | +84° | C |
| 16 | —N(Me)(cyclohexyl) | 1.5 | 3 | DC | 50 | 72 | — | EA-PE | 1.26 | 108-109 | +92.5° | A |
| 17 | —N((CH$_2$)$_7$)CH$_3$ | 1.5 | 3 | DC | 50 | 144 | — | PE | 1.18 | 151-153.5 | +92.6° | A$^2$ |
| 18 | —N((CH$_2$)$_8$)CH$_3$ | 1.5 | 2.5 | DC | 50 | 24 | — | EA-PE | 1.07 | 145-147 | +88.8° | A |
| 19 | —N(Me)CH$_2$CHCH$_2$CH$_3$ | 6.5 | 13 | MC | 150 | 8 | EA-PE | EA-PE | 0.83 | 108-110 | +90.7° | B |
| 20 | —NHCH$_2$CHCH$_2$CH$_3$ | 3.5 | 7 | MC | 100 | 18 | — | EA-PE | 1.7 | 104-106 | +91.4° | B |
| 21 | —NHC$_5$H$_{11}$ —NEt$_2$ | 1.2 | 2.4 | MC | 48 | 17 | — | DE-PE | 0.830 | 129-132 | +104° | B |
| 22 | —NPr$_2$ | 0.6 | 1.2 | MC | 24 | 18 | — | Ac-PE | 0.317 | 99-102 | +96.1° | B |

TABLE 1(a)-continued

| Ex. | —NR$^a$R$^b$ | Iodo-acetate (g) | Amine (ml) | Solvent | Vol (ml) | Reaction time (hrs) | TLC system | Crystallis-ation solvent | Yield (g) | m.p. (°C.) | [α]$_D$ c g/100 ml | Method of work-up |
|---|---|---|---|---|---|---|---|---|---|---|---|---|
| 23 | ![piperidine] | 0.6 | 1.2 | MC | 24 | 0.5 | — | DE-PE | 0.348 | 121-124 | +99° | B |
| 24 | 4-Me-piperidine | 0.6 | 1.2 | MC | 24 | 1.25 | — | DE-PE | 0.207 | 120-123 | — | E |
| 25 | —NHCH(Me)$_2$ / CMe | 5 | 10 (13) | ET | 100 | 16 | — | EA-PE | 3.33 | 123-126 | +97.0° | B |
| 26 | —NHCH$_3$ | 1 | 2 | ET | 10 | 72 | — | EA-PE | 0.3 | 164-168 | +105° | A |
| 27 | —NH Bu | 5 | 10 | ET | 100 | 16 | *EA | EA-PE | 2.29 | 78-80 | +99.0° | B |
| 28 | —NH$^i$ Pr | 1 | 2 | DC | 40 | 23 | *EA | M-W | 0.75 | 83-87 | +98.5° | B |
| 29 | | 1 | 2 | DC | 40 | 20 | *EA | M-W | 0.85 | 148-152 | +96° | C |
| 30 | —NH-cyclopentyl | 1 | 2 | DC | 40 | 23 | *EA | M-W | 0.81 | 79-82.5 | +92° | B |
| 31 | —NH-cyclohexyl | 5 | 10 | ET | 100 | 72 | *EA | EA-PE | 2.67 | 115-123 | +99° | B |
| 32 | —NHCHCH$_2$CH$_3$ / CH$_3$ | 5 | 10 | ET | 100 | 40 | *EA | DE-PE | 2.2 | 101-120 | +99° | B |
| 33 | —NHCH$_2$CH(CH$_3$)CH(CH$_3$)CH / CH$_3$ | 3 | 3 | ET | 50 | 15 | *EA | M-W | 1.60 | 48-88 | +90.0° | E(6) |
| 34 | —NHCH$_2$CH$_2$CH$_3$ | 2 | 1.5 | ET | 30 | 48 | EA | — | 1.63 | 148-151 | +92.9° | (8) |
| 35 | —NHCH$_2$C(CH$_3$)$_3$ | 2 | 1.5 | ET | 30 | 72 | *EA | — | .600 | — | +88.3° | B |
| 36 | —NHCH$_2$CH$_2$CH$_2$CH(CH$_3$)$_2$ | 2 | 2.0 | ET | 30 | 21 days | (9) | PE | .700 | 143-144 | +91.4° | (8) |
| 37 | —NHCH[CH(CH$_3$)$_2$]$_2$ —NH C$_8$H$_{17}$ | 1 | 2 | DC | 40 | 20 | *EA | M-W / PE | .451 | 82.5-87 | +100.5° | C |
| 38 | —NH-cyclopropyl | 1 | 2 | DC | 40 | 140 | EA | M-W | .569 | — | +79.2°(1.5) | A |

TABLE 1(a)-continued

| Ex. | —NR$^a$R$^b$ | Iodo-acetate (g) | Amine (ml) | Solvent | Vol (ml) | Reaction time (hrs) | TLC system | Crystallis-ation solvent | Yield (g) | m.p. (°C.) | [α]$_D$ c g/100 ml | Method of work-up |
|---|---|---|---|---|---|---|---|---|---|---|---|---|
| 39 | —NH-(adamantyl) | 1 | 2g | DC | 40 | 168 | * EA | EA EA-PE | .708 | 188–189 | +84.2° | C$^{(10)}$ |
| 40 | —N(CHCH$_2$CH$_3$)$_2$ CH$_3$ | 1.5 | 3 | DC | 50 | 8 weeks + 27 hrs reflux | Ac-PE | .204 | 135–140 | +90.5° | A$^{(11)}$ | |
| 41 | (2-methyl-piperidinyl) | .520 | 2 | MC | 20 | 3¼ | (3) EA | Ac/PE | .258 | 155–157 | +94° | F |
| 42 | (4-methyl-piperidinyl) | .800 | 2 | Ac | 30 | 1½ | (14) — | DE/PE | .497 | 134–138 | +96.3° | B$^{(12)}$ |
| 43 | —N(Et)(Bu) | .980 | 4 | MC | 30 | 24 | Ac-PE | — | .585 | — | +93° | C |
| 44 | —N(CH$_3$)$_2$ | .550 | 2 | MC | 20 | 2 | Ac/PE | DE/PE | .300 | 119–120 | +106° | F |
| 45 | —N(C$_2$H$_5$)$_2$ | .340 | 1.5 | MC | 15 | 2½ | EA | DE | .148 | 161–162 | +99° | F |
| 46 | —N(C$_3$H$_7$)$_2$ | .520 | 1 | MC | 20 | 4 weeks | EA | DE/PE | .168 | 154–158 | +96° | F |
| 47 | —(N$^n$C$_3$H$_7$)$_2$ | .510 | 2 | MC | 20 | 18 | EA/Ch | Ac/PE | .384 | 113–115 | +94° | F |
| 48 | (pyrrolidinyl) | .660 | 2.5 | MC | 25 | ⅜ | Ac/PE | — | .370 | — | +101° | F |
| 49 | (piperidinyl) | .550 | 2 | MC | 20 | 2 | Ac/PE | DE/PE | .320 | 135–136 | +99° | F |
| 50 | (tetrahydropyridinyl) | .510 | 2 | MC | 20 | 1½ | EA | — | .354 | — | +87° | F |
| 51 | (3-methyl-piperidinyl) | .510 | 2 | MC | 20 | 1½ | EA | — | .433 | — | +91° | F |

TABLE 1(a)-continued

| Ex. | —NR$^a$R$^b$ | Iodo-acetate (g) | Amine (ml) | Solvent | | Reaction time (hrs) | TLC system | Crystallis-ation solvent | Yield (g) | m.p. (°C.) | [α]$_D$ c g/100 ml | Method of work-up |
| --- | --- | --- | --- | --- | --- | --- | --- | --- | --- | --- | --- | --- |
| | | | | | Vol (ml) | | | | | | | |
| 52 | 4-methylpiperidine | .510 | 2 | MC | 20 | ½ | EA | EA/PE | .391 | 113–115 | +95° | F |
| 53 | pyrrolidine | .530 | 1 | MC | 20 | ½ | EA | DE/PE | .253 | 132–138 | +95° | F |
| 54 | 3-pyrroline | .530 | 1g | MC | 20 | 48 | EA/PE | DE | .411 | 173–174 | +87° | F |
| 55<br>56 | —N($^n$C$_3$H$_7$)$_2$<br>CH$_3$<br>\|<br>—NHCHCH$_2$CH$\diagdown$CH$_3$<br>$\diagup$CH$_3$ | .265<br>1.8 | 1<br>1.6g | MC<br>ET | 20<br>20 | 20<br>24 | Ch/M<br>— | —<br>DE-PE | .230<br>.710 | —<br>73–75 | +90.5°<br>+94.1° | F<br>E$^{(6)(7)}$ |
| 57 | 2R-ISOMER<br>CH$_3$<br>\|<br>—NHCHCH$_2$CH$\diagdown$CH$_3$<br>$\diagup$CH$_3$ | 1.2 | 1g | ET | 20 | 16 | — | EA-PE | .520 | 128–130 | +91.1° | E$^{(6)(7)}$ |
| 58 | 2S-ISOMER<br>—NHC(Me)$_3$ | 5 | 10 | ET | 100 | 168 | *EA | DE-PE | 1.63 | 102–110 | +150.5° | A |

TABLE 1(b)

| Ex. | —NR$^a$R$^b$ | Chloro- acetate (g) | Sodium iodide (g) | Amine (ml) | Solvent | Vol (ml) | Reaction time (hrs) | TLC system | Crystallisation solvent | Yield (g) | m.p. (°C.) | [α]$_D$ c g/ 100 ml | Method of work-up |
|---|---|---|---|---|---|---|---|---|---|---|---|---|---|
| 59 | —N⟨piperidine⟩-Me | .900 | .900 | 2 | Ac | 30 | 20 | *EA EA-PE | PE | .468 | 99–107 | +96° | A |
| 60 | —NHCH$_2$CH$_2$CH(CH$_3$)CH$_3$ | .900 | .450 | 1.8 | ET | 20 | 144 | *EA | DE | .454 | 156–164 | +91° | A |
| 61 | —NHCH(CH$_3$)CH$_2$CH(CH$_3$)CH$_3$ | .900 | .450 | 1.8 | ET | 20 | 144$^{(4)}$ | — | M/W | .771 | 120–124 | +90 | A |
| 62 | —N(C$_2$H$_5$)$_2$ | .500 | .500 | 1 | Ac | 20 | 24 | — | DE/PE | .412 | 147–154 | +100.1° | A |
| 63 | —N(Me)(Bu) | 1.0 | 1.0 | 4 | Ac | 30 | 48 | EA-Ch | DE/PE | .703 | 119–120 | +91.5° | C$^{(12)}$ |
| 64 | —N⟨piperidine⟩-ME | .900 | .900 | 2 | Ac | 30 | 20 | EA-PE | DE/PE | .673 | 103–115 | +87.7° | A |
| 65 | —N(Me)(Bu) | .600 | .600 | 1.2 | Ac | 12 | 20 mins$^{(5)}$ | EA | — | .403 | — | +94° | B |
| 66 | —N(C$_2$H$_5$)$_2$ | .500 | .500 | 1 | Ac | 35 | 72 | EA-PE | — | .433 | 124–125 | +79° | G |
| 67 | N(C$_2$H$_5$)$_2$ | .350 | .350 | 0.7 | ET | 10 | 72 | EA | — | .158 | 138–139 | +77.9° | H |
| 68 | —N(C$_2$H$_5$)$_2$ | .400 | .200 | 1 | Ac | 10 | 16¾ | — | EA-PE | .354 | 133–141 | +112° (1.4) | A |
| 69 | —N(Et)(Bu) | .400 | .200 | 1 | Ac | 10 | 17 | EA* | PE | .182 | 89–90.5 | +103° (0.51) | B |
| 70 | —N⟨piperidine⟩-Me | .400 | .200 | 1 | Ac | 10 | 17 | — | PE | .250 | 157–159 | +106° (0.6) | A |
| 71 | —N(C$_2$H$_5$)$_2$ | .300 | .300 | 0.6 | Ac | 20 | 72 | — | DE-PE | .203 | 113–114 | +110.7° | E$^{(6)(7)}$ |
| 72 | —N(Bu)(Me) | 1 | 1 | 2 | Ac | 30 | 17 | EA-PE | — | .875 | — | +77.9° | E$^{(6)}$ |
| 73 | —N⟨piperidine⟩-Me | .500 | .500 | 0.5 | Ac | 15 | 17 | EA-PE | DE-PE | .340 | 106.5–107.5 | +80.9° | E$^{(7)}$ |

*purified by column chromatography.
$^{(1)}$repeated TLC used.
$^{(2)}$the crude product was filtered through silica in ethyl acetate to remove colour before crystallising.
$^{(3)}$The product was triturated with ether before crystallisation.
$^{(4)}$Followed by 3 hours reflux.
$^{(5)}$Refluxed.
$^{(6)}$The residue was first diluted with water and extracted into ethyl acetate.
$^{(7)}$Basification effected with sodium hydroxide.
$^{(8)}$Water added to reaction mixture to precipitate product, which was then filtered, washed and dried.
$^{(9)}$Further purified by partitioning between ethyl acetate and hydrochloric acid and then ethyl acetate and sodium hydroxide.
$^{(10)}$Insoluble material in reaction mixture was removed by filtration prior to work-up.
$^{(11)}$The product was further purified by using work-up method E.
$^{(12)}$Ether used in place of ethyl acetate.
$^{(13)}$33% Solution of methylamine in ethanol.
$^{(14)}$The product was triturated with petroleum ether before crystallisation.

EXAMPLES 74–79

Preparation of 11β-aminoesters

Table 2 summarises the preparation of 11β-aminoesters by the following method:

The appropriate 11β-ester of 3α,11β-dihydroxy-5α-pregnan-20-one in the solvent indicated was treated with the appropriate amine for the time and at the temperature specified. In some cases sodium iodide was also present.

The reaction mixture was then worked up by one of the following methods:

A. The reaction mixture was partitioned between ethyl acetate and water and the washed and dried organic extract evaporated.

B. The solution was evaporated, the residue partitioned between sodium bicarbonate and ethyl acetate and the organic extract washed and evaporated.

C. The reaction mixture was diluted with water and the precipitated solid collected by filtration.

D. The reaction mixture was evaporated to low volume, the residue dissolved in chloroform, filtered and evaporated. Petrol was added and insoluble material removed. The mother liquor was partitioned between ether and hydrochloric acid, the acidic layer basified with NaOH and extracted with ether. The organic phase was washed, dried and evaporated.

The material obtained by one of these procedures was purified by preparative TLC and/or crystallisation.

TABLE 2

| Ex | 11β-substituent | Starting material wt (g) | Amine (ml) | Sodium iodide (g) | Solvent vol (ml) | Reaction Temp. | Reaction time | TLC system | Yield (g) | M.P. (°C.) | [α]_D c g/100 ml | Method of work-up |
|---|---|---|---|---|---|---|---|---|---|---|---|---|
| 74 | —OCOCH—N(CH₃)(4-CH₃-piperidine) | .350 | 2 | — | D 10 | Reflux | 40 hrs | Ac-PE | .160 | 166–171 | +94.8° (0.14) | A |
| 75 | —OCOCH—N(CH₃)(4-CH₃-piperidine) | .500 | 10 | — | — | Reflux | 18 hrs | EA-PE | .160 | 140–144 | +89° (0.16) | A |
| 76 | —OCO(CH₂)₃N(4-CH₃-piperidine) | .416 | 3 | — | — | 93° C. | 4 hrs | M-Ch | .376 | 93–98 | +81.8° | B |
| 77 | —OCOCHN(C₂H₅)₂(CH₃) | .500 | 4 | 1 | Ac 20 | Reflux | 3 days | EA-PE | .175 | 151–154 | +95.2° | A |
| 78 | —OCOCH—N(Me)(Bu)(CH₃) | .430 | 2 | .500 | Ac 30 | Reflux | 24 hrs | EA-PE | .085 | 100–105 | +87.7° | C |
| 79 | —OCOCH=CH₂, —OCOCH₂CH₂NHCHCH₂CH(CH₃)(CH₃) | .500 | 1 | — | — | R.T. | 3 hrs | — | .170 | 124–134 | +86.5° | D |

Crystallisation solvents
74, 75, 77 - DE-PE
76, 78 - M-W
79 - Ch-PE

EXAMPLES 80–100

N-Alkylation of 3α-hydroxy-11β-monoalkylamino- or aminoacyloxy-5α-pregnan-20-ones Table 3 summarises the preparation of 11β-aminoesters by one of the following methods:

A. The monoalkylamine was stirred at room temperature (unless otherwise stated) with an alkyl halide in ethanol (or excess halide) for the stated time. Some of the ethanol was evaporated and the residue partitioned between ethyl acetate and aqueous sodium carbonate solution, washed, dried and evaporated. The material was then chromatographed on silica gel and crystallised.

B. The monoalkylamine was heated at 100° C. with formic acid in 37% aqueous formaldehyde, the mixture cooled and partitioned between ethyl acetate and aqueous sodium bicarbonate solution. After extraction, washing and drying, the mixture was purified by chromatography and the product crystallised.

C. The monoalkylamine or amine was mixed with the appropriate aldehyde in ethanol, sodium cyanoborohydride added and after the time specified, the mixture was diluted with water and saturated sodium bicarbonate solution. The precipitated solid was collected by filtration, washed, dried and purified further by preparative TLC.

Examples 80–96 and 98–100 are 11β-aminoacetates and Example 97 is an 11β-3′-amino propionate.

TABLE 3

| Ex. | Substrate −NR$^a$R$^b$ | −NHR | wt (g) | Alkylating agent | vol (ml) | Method | Solvent | vol (ml) | Reaction time | Yield (g) | m.p. (°C.) | [α]$_D$ |
|---|---|---|---|---|---|---|---|---|---|---|---|---|
| 80 | −N(Me)(CH(CH$_3$)$_2$) (3) | −NHMe | 1.2 | (CH$_3$)$_2$CHI | 1 | A | ET | 50 | 60hrs at R.T. 72hrs at reflux | .170 | 95–107 | +94.1° |
| 81 | −N(Me)(C(CH$_3$)$_3$) | −NHC(CH$_3$)$_3$ | .900 | MeI | 0.46 | A | ET | 35 | 7 days | .280 | 143–147 | +95.3° |
| 82 | −N(Me)(C$_5$H$_{11}$) (4) | −NHC$_5$H$_{11}$ | .462 | MeI | 0.12 | A | ET | 12.5 | 28hrs | .103 | 75–78 | +90.0° |
| 83 | −N(Me)(CH$_2$CHCH$_2$CH$_3$ with CH$_3$) | −NHCH$_2$CHCH$_2$CH$_3$ (CH$_3$) | .750 | MeI | 30 | A | | | 2hrs | .140 | 108–111 | +90.5° |
| 84 | −N(Me)(CHCH$_2$CH$_2$CH$_3$ with CH$_3$) | −NHCH(CH$_3$)CH$_2$CH$_2$CH$_3$ | .462 | HCHO/HCO$_2$H | 2/0.08 | B | | | 5mins | .190 | 98–101 | +91.6° |
| 85 | −N(Me)(CH$_2$C(CH$_3$)$_3$) | −NHCH$_2$C(CH$_3$)$_3$ | .462 | HCHO/HCO$_2$H | 2/0.1 | B | | | 3mins | .210 | 142–144 | +93.2° |
| 86 | −N(Me)(C$_6$H$_{13}$) | −NHMe | 1.22 | C$_6$H$_{13}$I | 2 | A$^{(1)}$ | ET | 80 | 4hrs | .220 | 62–65 | +85.2° |
| 87 | −N(Me)(CCHCH$_2$CH with CH$_3$, CH$_3$, CH$_3$) (4) | −NHCH$_2$CH(CH$_3$)CH(CH$_3$)$_2$ | 1.06 | MeI | 1.5 | A$^{(6)}$ | ET | 24 | 18hrs | .360 | 82–89 | +86.7° |
| 88 | −N(Me)(CH$_2$CH=CH$_2$) | −NHMe | 1.22 | CH$_2$=CHCH$_2$Br | 0.67 | A$^{(2)}$ | ET | 50 | 1hr at R.T. 4.5hrs at reflux | .170 | 103–106 | +99° |

TABLE 3-continued

| Ex. | −NR$^a$R$^b$ | Substrate −NHR | wt (g) | Allylating agent | vol (ml) | Method | Solvent | vol (ml) | Reaction time | Yield (g) | m.p. (°C.) | [α]$_D$ |
|---|---|---|---|---|---|---|---|---|---|---|---|---|
| 89 | −N(Me)(CHCH$_2$CH$_2$CH(CH$_3$)CH$_3$) | −NHCHCH$_2$CH$_2$CH(CH$_3$)(CH$_3$) with CH$_3$ | .440 | HCHO/HCO$_2$H | 2/ 0.09 | B | W | 2 | 4mins | .200 | 54–66 | +84° |
| 90 | −N(Me)(cyclopropyl) | −NH-cyclopropyl | .389 | MeI | .24 | A | ET | 15 | 4days | .115 | 138–141 | +93.1° |
| 91 | −N(C$_2$H$_5$)(iC$_3$H$_7$) (3) | −NH$^i$C$_3$H$_7$ | .500 | C$_2$H$_5$I | 2 | A | ET | 50 | 14days | .104 | 143–146 | +94° |
| 92 | −N(C$_2$H$_5$)(CH$_2$CH(CH$_3$)(CH$_3$)) (3) | −NHCH$_2$CH(CH$_3$)(CH$_3$) | .900 | C$_2$H$_5$I | 3 | A$^{(2)}$ | ET | 50 | 72hrs at R.T. 48hrs at reflux | .120 | 127–133 | +93° |
| 93 | −N(C$_2$H$_5$)(CH$_2$CHCH$_2$CH$_3$ with CH$_3$) | −NHCH$_2$CHCH$_2$CH$_3$ with CH$_3$ | .231 | CH$_3$CHO/ NaBH$_3$CN | .06ml/ 100 mg | C | ET | 5 | 10mins | .136 | 108–110 | +86.7° |
| 94 | −N(C$_2$H$_5$)(CH$_2$CH(CH$_3$)(CH$_3$)) (3) | −NHCH$_2$CH(CH$_3$)(CH$_3$) | 1.13 | C$_2$H$_5$I | 3 | A$^{(2)}$ | ET | 50 | 72hrs at R.T. 48hrs at reflux | .140 | 127–135 | +86.6° |
| 95 | −N(Me)(CHCH$_2$CH(CH$_3$)(CH$_3$)) 2R-ISOMER | −NHCHCH$_2$CH(CH$_3$)(CH$_3$) 2R-ISOMER | .400 | HCHO/ HCO$_2$H | 2/ 0.08 | B | W | 2 | until effervescence ceased | .170 | 75–83 | +88° |
| 96 | −N(Me)(CHCH$_2$CH(CH$_3$)(CH$_3$)) 2S-ISOMER | −NHCHCH$_2$CH(CH$_3$)(CH$_3$) 2S-ISOMER | .400 | HCHO/ HCO$_2$H | 2/ 0.03 | B | W | 2 | until effervescence ceased | .150 | 73–85 | +84.8° |

TABLE 3-continued

| Ex. | −NR$^a$R$^b$ | Substrate −NHR | wt (g) | Alkylating agent | vol (ml) | Method | Solvent | vol (ml) | Reaction time | Yield (g) | m.p. (°C.) | [α]$_D$ |
|---|---|---|---|---|---|---|---|---|---|---|---|---|
| 97 | −N(Me)(CH$_3$)CHCH$_2$CH(CH$_3$)$_2$ | −NHCHCH$_2$CH(CH$_3$)CH$_3$ | .245 | HCHO/HCO$_2$H | 1/0.05 | B | W | 1 | 3mins | .180 | — | +88.7° |
| 98 | (piperidine, 5) | −NH$_2$ | .500 | CHO−(CH$_2$)$_3$−CHO NaBH$_3$CN | 1ml/250 mg | C | ET | 10 | 23hrs | .198 | — | +81° |
| 99 | −N(C$_2$H$_5$)$_2$ | −NH$_2$ | .500 | CH$_3$CHO/NaBH$_3$CN | 0.5ml/250 mg | C | ET | 10 | 3hrs | .109 | 133–142 | +95.5° |
| 100 | −N(CH$_2$CHCH$_2$CH$_3$)(CH$_3$) | −NHCHCH$_2$CH$_3$(CH$_3$) | 1.34 | CH$_3$I | 0.74 | A | ET | 50 | 7 days | .340 | 120–125 | +96.1° |

| TLC system | Crystallisation Solvents |
|---|---|
| 80 - ET-EA  83, 84, 85 - EA-PE | 80, 83, 84, 85 - DE-PE |
| 82 - EA  86, 81 - EA | 82, 86 - PE |
| Ac-PE | 81 - EA-PE |
| 88, 91 - EA | 87 - M-W |
| 89, 90 - EA-PE | 88, 89, 90, 91 - DE-PE |
| 92, 94 - EA | 92, 93, 94 - DE-PE |
| EA-PE | 95, 96 - DE-PE |
| 93 - EA-PE | M-W |
| 95, 96 - EA-PE | |
| EA | |
| 97 - ET-EA | 99 - PE |
| 98, 99, 100 - EA | 100 - EA-PE |

[1] Reflux.
[2] Reaction started at room temperature and then refluxed.
[3] Calcium carbonate present in reaction mixture.
[4] Potassium carbonate present in reaction mixture.
[5] 0.1 ml Acetic acid present in reaction mixture.
[6] Purified by column chromatography in ethyl acetate.

EXAMPLE 101

2β-Ethoxy-11β-diethylaminoacetoxy-3α-hydroxy-5α-pregnan-20-one and its citrate salt Diethylamine (4 ml) was added to a solution of 2β-ethoxy-3α-hydroxy-11β-iodoacetoxy-5α-pregnan-20-one (775 mg) in methylene chloride (20 ml) and the mixture was kept at room temperature for 3.5 hours. The solvent was evaporated in vacuo and the residue was partitioned between ethyl acetate and water. Evaporation of the washed organic layer gave a froth (707 mg) which was purified by preparative TLC (5% MeOH in CHCl₃) and crystallization of the major band (674 mg) from ether-petroleum ether to yield title compound (580 mg), m.p. 125°–126°.

A solution of the above free base (492 mg; 1 mmole) in ethanol (10 ml) was treated with a solution (10 ml) of M/10 citric acid in ethanol water (9:1) and the mixture evaporated in vacuo at low temperature to afford a froth. This froth, which dissolved readily in saline, was bulked up to 49.2 g by the addition of saline. The resulting solution of the citrate salt, which was 1% with respect to steroid base, had a pH of 3.5.

EXAMPLE 102

2β-Chloro-11β-diethylaminoacetoxy-3α-hydroxy-5α-pregnan-20-one

A solution of 11β-diethylaminoacetoxy-2α,3α-epoxy-5α-pregnan-20-one (800 mg) in concentrated hydrochloric acid (6 ml) was kept at room temperature for 15 minutes and then diluted with a large excess of sodium bicarbonate solution. The precipitated solid (767 mg) was collected by filtration and purified by preparative TLC (ethylacetate) and crystallization from petroleum ether to afford title compound, (305 mg). m.p. 182°–187°, $[\alpha]_D+101.4°$.

EXAMPLE 103

2β-chloro-3α-hydroxy-11β-4'-methylpiperidinoacetoxy-5α-pregnan-20-one

Using 2α,3α-epoxy-11β-4'-methylpiperidinoacetoxy-5α-pregnan-20-one (1 g) and concentrated hydrochloric acid (8 ml) the procedure of Example 102 was repeated to afford title compound (378 mg), m.p. 159°–166°, $[\alpha]_D+94°$. (crystallised from ether-petrol).

EXAMPLE 104

11β-Diethylaminoacetoxy-3α-hydroxy-2β-thiocyanato-5α-pregnan-20-one

Syrupy phosphoric acid (13.8 g) was added to a solution of potassium thiocyanate (9.2 g) in ice water covered by a layer of ether (30 ml). After extraction of the thiocyanic acid the pink ethereal layer was dried over sodium sulphate. A portion (34 ml) of this solution (total volume 50 ml) was added to 11β-diethylaminoacetoxy-2α,3α-epoxy-5α-pregnan-20-one (786 mg) in sodium dried ether (about 20 ml) with good stirring. The mixture was stirred overnight and then poured into saturated sodium bicarbonate solution and extracted into ethyl acetate. The washed and dried extract was evaporated in vacuo and the residual white solid purified by preparative TLC (ethyl acetate) and crystallization from ether-petroleum ether to give title compound (591 mg), m.p. 173°–180°. $[\alpha]_D+100°$.

EXAMPLE 105

11β-N-Butyl-N-methylaminoacetoxy-3α-hydroxy-5α-androstane-17β-carbonitrile

N-Methyl-N-butylamine (2 ml) was added to 3α-acetoxy 11β-iodoacetoxy-5α-androstane-17β-carbonitrile (1 g) in methylene chloride (20 ml). The mixture was kept overnight at room temperature and then diluted with ethyl acetate, washed with sodium bicarbonate solution, water, dried and evaporated in vacuo to give 3α-acetoxy-11β-N-butyl-N-methylaminoacetoxy-5α-androstane-17β-carbonitrile. This material in methanol (80 ml) was treated with sodium bicarbonate (1 g) in water (20 ml) and refluxed for 3 hours, more sodium bicarbonate (1 g) in water (20 ml) being added after 2 hours. Dilution of the cooled mixture with water and extraction with ethyl acetate afforded a product which was crystallized from ether-petroleum ether to give title compound, m.p. 108°–110°, $[\alpha]_D+51°$.

EXAMPLE 106

3α-Hydroxy-11β-dipropylaminoacetoxy-5α-androstane-17β-carbonitrile

Using dipropylamine (2 ml) in place of N-methyl-N-butylamine and a reaction time of 3 days, the general procedure of Example 105 was followed to yield title compound (373 mg) m.p. 114°–116°, $[\alpha]_D+49°$.

EXAMPLE 107

2β-Bromo-11β-(N-butyl-N-methylaminoacetoxy)-3α-hydroxy-5α-pregnan-20-one

A mixture of 11β-(N-butyl-N-methylaminoacetoxy)-2α,3α-epoxy-5α-pregnan-20-one (1.6 g) and aqueous 47% hydrobromic acid (2 ml) in chloroform (100 ml) was stirred at room temperature for 1 hour. The solution was washed with dilute sodium bicarbonate solution and water, dried and evaporated in vacuo to give a foam. Crystallization from ethyl acetate-petroleum ether afforded title compound, m.p. 108°–110°, $[\alpha]_D+95°$ (1.303 g).

EXAMPLE 108

2β-Bromo-11β-N,N-diethylaminoacetoxy-3α-hydroxy-5α-pregnan-20-one

Using 11β-N,N-diethylaminoacetoxy-2α,3α-epoxy-5α-pregnan-20-one (1.6 g) the method of Example 107 was repeated to afford title compound (1.01 g) m.p. 149°–150°, $[\alpha]_D+96.5°$.

EXAMPLE 109

21-Acetoxy-3α-hydroxy-11β-dipropylaminoacetoxy-5α-pregnan-20-one

Lead tetra-acetate (8 g) was added to a solution of 11β-dipropylaminoacetoxy-3α-hydroxy-5α-pregnan-20-one (4 g) in benzene (144 ml) containing methanol (9.2 ml) followed by boron trifluoride etherate (22.8 ml). The mixture was kept at 10° for 4 hours and then poured into excess sodium bicarbonate solution. Extraction with ether and evaporation in vacuo of the washed and dried (sodium sulphate) organic extract afforded the product which was purified by preparative TLC in ethyl acetate-petroleum ether (1:1) and crystallisation from ether-petroleum ether to yield title compound, m.p. 159°–161°.

EXAMPLE 110

Preparation of 11β-diethylaminoacetoxy-3α-hydroxy-5α-pregnan-20-one in various solvents 3α-Hydroxy-11β-iodoacetoxy-5α-pregnan-20-one (50 mg) in the appropriate solvent (see Table 4) was treated with diethylamine (0.2 ml) and the resulting mixture was kept at room temperature.

The reaction was monitored by TLC over silica using acetone-petroleum ether (1:2) or methanol-chloroform (1:19) as solvent and the identity of the product was similarly checked by TLC.

TABLE 4

| Solvent | Approximate time for complete reaction |
| --- | --- |
| Acetone | 2.5 hours |
| Ethanol | 48 hours |
| Dimethylforamide | 4 hours |
| Acetonitrile | 4 hours |
| Ether | 48 hours |
| Tetrahydrofuran | 4 hours |
| Ethyl acetate | 24 hours |
| Toluene | 24 hours |

EXAMPLE 111

11β-(N-Butyl-N-methylaminoacetoxy)-3α-hydroxy-5α-pregnan-20-one and its citrate salt A solution of 3α-hydroxy-11β-iodoacetoxy-5α-pregnan-20-one (1.5 g) in 1,2-dichloroethane (60 ml) was treated with N-methyl-N-butylamine (3 ml) and the mixture was kept at room temperature for 4 hours. Evaporation of the solvent afforded an oil which was triturated with water to give a yellow solid. Purification by chromatography over silica in ethyl acetate and crystallisation from petroleum ether afforded title compound (1.14 g), m.p. 93°-94°, $[\alpha]_D+97.5°$.

The above free base (500 mg) was added to a solution of citric acid (228 mg) in 0.9% w/v sodium chloride solution. The solution was adjusted to pH 4.0 by the addition of sodium hydroxide solution and then more sodium chloride solution was added to give a final volume of 50 ml. This 1% solution of the citrate salt was then filtered through a membrane.

EXAMPLE 112

3α,21-Dihydroxy-11β-N,N-dipropylaminoacetoxy-5α-pregnan-20-one

21-Acetoxy-11β-N,N-dipropylaminoacetoxy-3α-hydroxy-5α-pregnan-20-one (800 mg) in methanol (16 ml) was refluxed with 20% aqueous potassium hydrogen carbonate solution (4 ml) under nitrogen for 1 hour. The mixture was poured into ice-water and extracted with ethyl acetate. The organic layer was washed, dried and evaporated. The residue was purified by preparative TLC (ethyl acetate-petroleum ether b.p. 40°-60° (2:1)×2) and triturated with pentane to give title compound (219 mg) m.p. 98°-102°, $[\alpha]_D+66°$.

EXAMPLE 113

11β-N,N-Dipropylaminoacetoxy-3α-hydroxy-5α-pregnan-20-one

11β-N,N-Dipropylaminoacetoxy-3β-hydroxy-5α-pregnan-20-one (110 mg) was stirred with triphenylphosphine (364 mg) and formic acid (0.1 ml) in tetrahydrofuran (5 ml.) and diethylazodicarboxylate (240 mg) added. Further reagent (5 drops) was added until a good yellow colour persisted. After 16 hours the mixture was concentrated and filtered through silica gel (20 g) in ethyl acetate: petroleum ether (1:1). Evaporation of the eluate gave a residue which was purified by preparative TLC (ethyl acetate: petroleum ether (1:1)) to give 11β-N,N-dipropylaminoacetoxy-3α-formyloxy-5α-pregnan-20-one (30 mg), $[\alpha]_D+73°$.

The above formate (26 mg) was stored at 21° with 60% aqueous perchloric acid (0.1 ml) in methanol (3 ml) for 30 minutes. The mixture was partitioned between ethyl acetate and excess sodium hydrogen carbonate solution. The aqueous layer was extracted with further ethyl acetate and the combined organic layers were washed with brine and dried with sodium sulphate. After concentration, the the product was purified by column chromatography in mixtures of ethyl acetate and petroleum ether. Concentration of the eluate gave a residue which was further purified by preparative TLC (ethyl acetate) to give title compound (7 mg) which was identical by TLC (ethyl acetate), to the product of Example 1.

EXAMPLE 114

11β-Diethylaminoacetoxy-3α-hydroxy-5α-pregn-1-en-20-one

2β-Bromo-11β-diethylaminoacetoxy-3α-hydroxy-5α-pregnan-20-one (1 g) was stirred and warmed with dihydropyran (2 ml) in benzene (40 ml) containing p-toluene sulphonic acid monohydrate (406 mg) until a clear solution was achieved. After 20 mins, the mixture was washed with excess sodium bicarbonate solution and brine (2x) and dried with magnesium sulphate. Evaporation of the benzene left a gum which was dissolved in N,N-dimethylformamide (25 ml) and stirred at 120° with calcium carbonate (2.5 g) and lithium bromide (3.3 g) for 5.5 hours. When reaction was complete, the mixture was diluted with methanol and filtered. The methanolic filtrate was made acidic by addition of 2N hydrochloric acid (4 ml). After 4 hours at 20°, excess sodium bicarbonate solution was added and the mixture evaporated to a small volume, extracted with ethyl acetate (twice) and the combined organic solutions were washed with brine (twice) and dried with magnesium sulphate. Evaporation of the solvent left a gum which was filtered through silica gel (30 g) in ethyl acetate and the eluate concentrated. Further purification was achieved by preparative TLC and recrystallisation from aqueous methanol to give title compound m.p. 134°-138°, $[\alpha]_D+51.6°$ (270 mg).

EXAMPLE 115

11β-(N-Butyl-N-ethylaminoacetoxy)-3α-hydroxy-5α-pregnan-20-one

3α-Hydroxy-11β-iodoacetoxy-5α-pregnan-20-one (1.5 g) was stirred with N-butyl-N-ethylamine (3 ml) in dichloromethane (60 ml) at 20° for 21 hours. The solution was washed with water and the solvent was evaporated at reduced pressure. The residue was triturated with water giving a solid which was recrystallised from aqueous methanol to give title compound (1.2 g), m.p. 111°-112.5°, $[\alpha]_D+93.5°$.

EXAMPLES 116-222

Preparation of salts

Table 5 summarises the properties and preparation of salts of the invention by one of the following methods:

A. The 11β-aminoester (1 part) was added to a solution of the acid (1 molar part) in water and the mixture stirred or shaken until a clear solution was obtained. The solution was made up with water to the weight indicated, filtered through a membrane and the pH determined.

B. The 11β-aminoester (1 part) was added to a solution of the acid (1 molar part) in water and the mixture stirred or shaken. As free base remained undissolved, further acid was added and the mixture agitated again. The solution was made up with water to the weight indicated and any material which then remained undissolved was collected in a weighed funnel and the weight of free base dissolved calculated and the pH of the solution measured.

C. A mixture of the 11β-aminoester (1 part), a 0.1 M solution of the acid (1 molar part) and ethanol was evaporated in vacuo and dried to constant weight. The residue was dissolved in a little water and any material which then remained undissolved collected in a weighed funnel and the weight of free base dissolved calculated. The solution was made up with water to the weight indicated and its pH measured.

D. The 11β-aminoester (1 part) was added to a solution of the acid (1 molar part) in water and the mixture stirred or shaken. The solution was made up with water to the weight indicated. The material remaining undissolved was collected in a weighed funnel and the weight of free base dissolved calculated and the pH of the solution measured.

E. As in method C except that further acid was added to the residue after addition of the small amount of water.

The solid citric acid used was as its monohydrate.

TABLE 5

| Ex | Free base Ex.No. | Salt | Method | Dissolved aminoester(mg) | Acid | WT. of solution (g) | pH | Ethanol (ml) |
|---|---|---|---|---|---|---|---|---|
| 116 | 4 | citrate | A | 100 | 48.4 mg | 10 | 3.63 | — |
| 117 | 5 | citrate | A | 100 | 48.9 mg | 10 | 3.4 | — |
| 118 | 6 | citrate | C[7] | 38 | 89 mg | 10 | 2.55 | 3 |
| 119 | 8 | citrate | B | 73 | 85 mg | 10 | 2.7 | — |
| 120 | 9 | citrate | C | 87 | 2 ml[1] | 10.4 | 3.5 | — |
| 121 | 10 | citrate | A | 120 | 49.7 mg | 12 | 3.65 | — |
| 122 | 11 | citrate | A | 375 | 143 mg | 37.5[2] | 3.5 | — |
| 123 | 12 | citrate | A | 122 | 53 mg | 12.3 | 3.6 | — |
| 124 | 13 | citrate | A | 75 | 33 mg | 7.5 | 3.65 | — |
| 125 | 14 | citrate | B | 98 | 88 mg | 10 | 2.82 | — |
| 126 | 15 | citrate | B | 56 | 32 mg | 10 | 2.65 | — |
| 127 | 16 | citrate | A | 100 | 43 mg | 10 | 3.62 | — |
| 128 | 17 | citrate | B | 68 | 88 mg | 10 | 2.65 | — |
| 129 | 19 | citrate | A | 92.3 | 42 mg | 10.3 | 3.64 | — |
| 130 | 20 | citrate | B | 80 | 63 mg | 9.2 | 3.12 | — |
| 131 | 21 | citrate | A | 100 | 45 mg | 10 | 3.55 | — |
| 132 | 22 | citrate | A | 100 | 42.9 mg | 10 | 3.4 | — |
| 133 | 23 | citrate | A | 100 | 44.4 mg | 10 | 3.7 | — |
| 134 | 24 | citrate | D | 84 | 43 mg | 10 | 3.2 | — |
| 135 | 25 | citrate | A | 80.5 | 42 mg | 8.95 | 3.27 | — |
| 136 | 27 | citrate | D | 83.5 | 42 mg | 8.95 | 3.60 | — |
| 137 | 29 | citrate | A | 100 | 46 mg | 10 | 3.62 | — |
| 138 | 30 | hydrochloride | A | 100 | 2.12[3] ml | 10 | 3.10 | — |
| 139 | 31 | citrate | A | 89.5 | 42 mg | 8.95 | 3.76 | — |
| 140 | 32 | citrate | D | 80.7 | 42 mg | 9.52 | 3.59 | — |
| 141 | 33 | citrate | B | 77.3 | 84 mg | 9.2 | 2.89 | — |
| 142 | 34 | citrate | B | 92.3 | 63 mg | 9.23 | 3.12 | — |
| 143 | 35 | citrate | B | 86 | 84 mg | 9.8 | 2.85 | — |
| 144 | 36 | citrate | B | 61 | 84 mg | 9.8 | 2.79 | — |
| 145 | 38 | citrate | D | 93 | 68.5 mg | 10 | 2.93 | — |
| 146 | 39 | citrate | B | 86 | 80 mg | 10 | 2.92 | — |
| 147 | 40 | citrate | B | 85 | 93 mg | 10 | 2.03 | — |
| 148 | 41 | citrate | C | 95.4 | 2 ml | 9.54 | 3.55 | 2 |
| 149 | 42 | citrate | B | 106 | 84 mg | 10.6 | 2.9 | — |
| 150 | 43 | citrate | A | 120 | 48.5 mg | 12 | 3.35 | — |
| 151 | 44 | citrate | A | 100 | 50 mg | 10 | 3.6 | — |
| 152 | 45 | citrate | C | 55.95 | 1.25 ml | 5.6 | 3.6 | 1.5 |
| 153 | 46 | citrate | B | 79 | 70 mg | 7.9 | 3.02 | — |
| 154 | 47 | citrate | C | 91 | 2 ml | 9.1 | 3.5 | 2 |
| 155 | 48 | citrate | C | 87.7 | 2 ml | 8.77 | 3.45 | 2 |
| 156 | 49 | citrate | C | 90.3 | 2 ml | 9.06 | 3.52 | 2 |
| 157 | 51 | citrate | C | 95 | 2 ml | 9.5 | 3.59 | 2 |
| 158 | 52 | citrate | C | 93.8 | 2 ml | 9.38 | 3.60 | 2 |
| 159 | 53 | citrate | C | 91.7 | 2 Ml | 9.17 | 3.55 | 2 |
| 160 | 54 | citrate | E | 80.6 | 4 ml | 6.12 | 2.6 | 4 |
| 161 | 55 | citrate | E | 78 | 4 ml | 7.8 | 2.8 | 2 |
| 162 | 56 | citrate | B | 86 | 84 mg | 9.5 | 3.0 | — |
| 163 | 57 | citrate | B | 68 | 60 mg | 68 | 3.08 | — |
| 164 | 59 | citrate | A | 103.5 | 42 mg | 10.35 | 3.72 | — |
| 165 | 60 | citrate | D | 76.5 | 42 mg | 10.1 | 3.68 | — |
| 166 | 61 | citrate | B | 104 | 63 mg | 10.4 | 3.28 | — |
| 167 | 62 | citrate | D | 93 | 42 mg | 10.1 | 3.65 | — |
| 168 | 63 | citrate | B | 70.5 | 168 mg | 10.7 | 2.4 | — |
| 169 | 64 | citrate | B | 80.5 | 84 mg | 10.9 | 2.8 | — |
| 170 | 65 | citrate | A | 104 | 42 mg | 10.4 | 3.7 | — |
| 171 | 66 | citrate | A | 100 | 46 mg | 10 | 3.4 | — |
| 172 | 67 | citrate | A | 100 | 40.2 mg | 10 | 3.2 | — |

TABLE 5-continued

| Ex | Free base Ex.No. | Salt | Method | Dissolved amino-ester(mg) | Acid | WT. of solution (g) | pH | Ethanol (ml) |
|---|---|---|---|---|---|---|---|---|
| 173 | 68 | citrate | B | 78 | 91 mg | 10 | 2.82 | — |
| 174 | 69 | citrate | B | 100 | 85.6 mg | 10 | 2.90 | — |
| 175 | 70 | citrate | B | 95 | 86 mg | 10 | 2.96 | — |
| 176 | 71 | citrate | A | 103 | 46 mg | 10 | 3.7 | — |
| 177 | 72 | citrate | A | 100 | 44 mg | 10 | 4.0[4] | — |
| 178 | 73 | citrate | A | 100 | 43 mg | 10 | 3.6 | — |
| 179 | 74 | citrate | C | 96.5 | 2.5ml[1] | 9.65 | 3.66[4] | — |
| 180 | 75 | citrate | C | 117 | 2.5ml[1] | 11.7 | 3.60 | — |
| 181 | 76 | citrate | A | 101 | 42 mg | 10.04 | 3.72 | — |
| 182 | 78 | citrate | C | 49 | 1.3ml[1] | 4.9 | 3.43 | — |
| 183 | 80 | citrate | B | 57.5 | 84 mg | 8.05 | 2.69 | — |
| 184 | 100 | citrate | B | 94.5 | 84 mg | 9.83 | 3.0 | — |
| 185 | 82 | citrate | B | 65.3 | 64 mg | 7.1 | 2.86 | — |
| 186 | 83 | citrate | B | 75 | 63 mg | 9.3 | 2.85 | — |
| 187 | 84 | citrate | A | 95 | 42 mg | 9.5 | 3.63 | — |
| 188 | 85 | citrate | B | 31 | 84 mg | 9.5 | 2.58 | — |
| 189 | 86 | citrate | B | 93 | 84 mg | 9.8 | 2.98 | — |
| 190 | 87 | citrate | D | 86 | 42 mg | 9.8 | 3.43 | — |
| 191 | 88 | citrate | D | 86.1 | 42 mg | 8.9 | 3.20 | — |
| 192 | 89 | citrate | B | 100.7 | 84 mg | 10.07 | 3.00 | — |
| 193 | 90 | citrate | B | 23 | 90 mg | 6.4 | 2.46 | — |
| 194 | 91 | citrate | D | 57 | 30 mg | 6.6 | 3.56 | — |
| 195 | 92 | citrate | B | 59 | 60 mg | 6.8 | 2.98 | — |
| 196 | 93 | citrate | B | 39 | 60 mg | 7 | 2.53 | — |
| 197 | 94 | citrate | B | 63 | 60 mg | 7.2 | 2.99 | — |
| 198 | 95 | citrate | D | 90 | 42 mg | 9.8 | 3.62 | — |
| 199 | 96 | citrate | B | 88 | 63 mg | 9.8 | 3.12 | — |
| 200 | 97 | citrate | B | 83 | 63 mg | 10.1 | 3.2 | — |
| 201 | 81 | citrate | B | 98.3 | 84 mg | 9.83 | 3.12 | — |
| 202 | 102 | citrate | C | 120.5 | 2.5 ml[1] | 12.05 | 3.65 | — |
| 203 | 103 | citrate | E | 127 | 2.5 ml[1] +52 mg | 12.7 | 2.85 | — |
| 204 | 104 | citrate | D | 88.7 | 42 mg | 10.09 | 3.5 | — |
| 205 | 105 | citrate | D | 97 | 47.3mg | 10 | 3.4 | — |
| 206 | 106 | citrate | B | 84 | 91.6mg | 15 | 2.7 | — |
| 207 | 107 | citrate | B | 59 | 78 mg | 10 | 2.6 | — |
| 208 | 108 | citrate | B | 65 | 80 mg | 10 | 2.6 | — |
| 209 | 109 | citrate | D | 75 | 39.4 mg | 10 | 3.2 | — |
| 210 | 112 | citrate | A | 100 | 42.7 mg | 10.2 | 3.7 | — |
| 211 | 114 | citrate | D | 94 | 47 mg | 10 | 3.2 | — |
| 212 | 47 | glutarate | E | 73 | 5 ml | 12.125 | 3.6 | 2 |
| 213 | 47 | hydro-chloride | C | 119 | 2.5ml | 12 | 3.8 | 2 |
| 214 | 47 | hemi-sulphate | C | 115 | 2.5ml | 11.5 | 3.52 | 2 |
| 215 | 47 | dihydrogen phosphate | C | 111 | 2.5ml | 11.1 | 3.63 | 2 |
| 216 | 47 | tartrate | C | 116 | 2.5ml | 11.6 | 3.58 | 2 |
| 217 | 47 | lactate | C | 76 | 5ml | 12.1 | 3.53 | 2 |
| 218 | 47 | tricarbal-lylate | C | 951 | 40ml | 95[2] | 3.38 | 18 |
| 219 | 47 | mesylate | D | 106 | 2.3ml[5] | 10.6 | 3.77 | — |
| 220 | 115 | tricarball-ylate | E | 100 | 2.1ml +37mg[6] | 10 | 3.6 | 2 |
| 221 | 115 | hydro-chloride | A | 150 | 3.15ml[3] | 15 | 3.52 | — |
| 222 | 115 | citrate | A | 500 | 221 mg | 50[2] | 3.97[4] | — |

[1] 0.1 M citric acid solution (10% water in ethanol).
[2] Solution prepared using 0.9% w/v saline in place of water.
[3] 0.1 M Hydrochloric acid solution.
[4] pH adjusted with sodium hydroxide solution.
[5] 0.1 M methanesulphonic acid.
[6] 0.1 M 90% ethanolic tricarballylic acid solution.
[7] 2 Molar equivalents of citric acid used initially.

EXAMPLE 223

11β-N,N-Diethylaminoacetoxy-2β-ethoxy-3α-hydroxy-5α-pregnan-20-one, citrate salt 11β-N,N-Diethylaminoacetoxy-2β-ethoxy-3α-hydroxy-5α-pregnan-20-one (1.45 g) was agitated with citric acid monohydrate (621 mg) in 0.9% w/v sodium chloride solution (steriflex(R)) (130 ml.) at 20° for 16.5 hours. The resulting solution was stirred at 21° and N/5 sodium hydroxide solution in steriflex(R) (10.5 ml) was added dropwise during 30 minutes, raising the pH from 3.63 to 4.52. The solution was diluted to 162.5 g so that the concentration of steroid was 9 mg/ml. The solution of the citrate was filtered through a membrane and finally filtered into 8 sterile ampoules.

EXAMPLE 224

11β-(N-Butyl-N-ethylaminoacetoxy)-3α-hydroxy-5α-pregnan-20-one, citrate salt

11β-(N-Butyl-N-ethylaminoacetoxy)-3α-hydroxy-5α-pregnan-20-one (1.80 g) was agitated with citric acid monohydrate (793 mg) in 0.9% w/v sodium chloride solution (steriflex$^{(R)}$) (160 ml) at 20° for 19.5 hours. The resulting solution was slightly cloudy. This solution was stirred at 21° and N/5 sodium hydroxide solution in steriflex$^{(R)}$ (5.8 ml) was added dropwise during 15 minutes, raising the pH from 3.62 to 4.00. The solution was diluted to 201.2 g so that the concentration of steroid was 9 mg/ml. The cloudiness was removed by filtration through a membrane and the clear solution of the citrate was filtered into 8 sterile ampoules.

EXAMPLE 225

11β-Diethylaminoacetoxy-2β-ethoxy-3α-hydroxy-D-homo-5α-pregnan-20-one, and its citrate salt Sodium iodide (0.250 g) and diethylamine (0.5 ml) were added to a solution of 11β-chloroacetoxy-2β-ethoxy-3α-hydroxy-D-homo-5α-pregnan-20-one (0.250 g) in acetone (10 ml) and the mixture was left at room temperature for 3 days during which time a white solid precipated. Water was added and the yellow solution was concentrated in vacuo whereupon crystallisation occurred. The needles were filtered off and washed well with acetone/water yielding the title compound (0.201 g), m.p. 160°-73°, $[\alpha]_D+60.8°$. The above base (0.101 g) was stirred with citric acid monohydrate (0.042 g) in water (9.5 ml) for 21 hours. The solution was made up to 10.1 g by weight. The solid remaining out of solution was filtered off, dried and weighed. The solution was passed through a millipore filter giving an aqueous solution of the title compound, concentration 9.75 mg/ml, pH 3.66.

EXAMPLE 226

11β-Dipropylaminoacetoxy-2β-ethoxy-3α-hydroxy-D-homo-5α-pregnan-20-one, and its citrate salt Sodium iodide (0.24 g) and dipropylamine (0.5 ml) were added to a solution of 11β-chloroacetoxy-2β-ethoxy-3α-hydroxy-D-homo-5α-pregnan-20-one (0.240 g) in acetone (10 ml) and the mixture was left at room temperature for 2 days. The mixture was then partitioned between ethyl acetate and water and the ethyl acetate solution washed many times with water. The organic solution was dried over anhydrous sodium sulphate and evaporated to a yellow foam (0.233 g). Preparative t.l.c. in ethyl acetate/petrol 3:1 gave a white foam (0.190 g) which was crystallised from methanol/water yielding the title compound as white needles (0.147 g), m.p. 150°-9°, $[\alpha]_D+56.8°$.

The above base (0.096 g) was stirred in a solution of citric acid monohydrate (0.038 g) in water (8.5 ml) for 20 hours. A large proportion of the steroid remained out of solution. More citric acid (0.038 g) was added and the mixture stirred for a further 6 hours. The solution was made up to 9.6 g by weight and the solid remaining out of solution was filtered off, dried and weighed. The solution was passed through a millipore filter giving an aqueous solution of the title compound, concentration 9.5 mg/ml, pH 2.85.

EXAMPLE 227

11β-Dipropylaminoacetoxy-3α-hydroxy-19-nor-5α-pregnan-20-one and its citrate salt A solution of 11β-chloroacetoxy-3α-hydroxy-19-nor-5α-pregnan-20-one (0.330 g) in acetone (12 ml) was treated with NaI (0.330 g) and dipropylamine (0.7 ml) for 20 hrs at room temperature. The reaction mixture was diluted with water to dissolve the precipitate and evaporated to low volume. The residue was partitioned between ethyl acetate and 2N hydrochloric acid (25 ml). The ethyl acetate layer was extracted twice more with 2N hydrochloric acid (25 ml). The acid fractions were combined and basified to pH 10 with 2N NaOH solution and the white precipitate was extracted into ethyl acetate. The organic solution was washed with water until the washings remained at neutral pH, was dried over anhydrous sodium sulphate and evaporated to give a sticky foam (0.283 g). This was crystallised from methanol/water yielding the title compound as plates (0.207 g) (54%), m.p. 108°-111°, $[\alpha]_D+100.3°$.

To a solution of citric acid monohydrate (52.5 mg) in water (2 ml) was added the above free base (115 mg). More water (8 ml) was added and the mixture was stirred for 72 hrs. A small amount of steroid remained out of solution and more citric acid (52.5 mg) was added. Within 5 mins. a clear solution was obtained which was made up to 11.5 g with water and filtered through a millipore filter yielding an aqueous solution of the title citrate, concentration 10 mg/ml, pH 3.0.

EXAMPLE 228

11β-N-Butyl-N-methylaminoacetoxy-3α-hydroxy-19-nor-5α-pregnan-20-one and its citrate salt Sodium iodide (0.330 g) and N-methylbutylamine (0.7 ml) were added to a solution of 11β-chloroacetoxy-3α-hydroxy-19-nor-5α-pregnan-20-one (0.330 g) in acetone (12 ml). The mixture was left at room temperature for 24 hrs. It was then diluted with water to dissolve the precipitate. The orange solution was evaporated and the residue was partitioned between ethyl acetate and 2N hydrochloric acid (25 ml). The ethyl acetate layer was extracted twice more with 2N hydrochloric acid (25 ml) and the acid fractions were combined and basified to pH 10 with 2N NaOH solution. The precipitated steroid was extracted into ethyl acetate (twice) and the ethyl acetate extracts were combined and washed with water until the washings remained at neutral pH. The organic solution was dried over anhydrous sodium sulphate and evaporated to a solid (0.314 g). This was crystallised from ether/petrol to give the title compound as needles (0.268 g) (72%), m.p. 94°-95°, $[\alpha]_D+104°$.

The above free base (112 mg) was added to a solution of citric acid monohydrate (52.5 mg) in water (2 ml). More water (8 ml) was added and the mixture was swirled from time to time. After 30 mins. complete solution was obtained. The weight of the solution was increased to 11.2 g with water and the resulting solution was filtered through a millipore filter yielding an aqueous solution of the title citrate, concentration 10 mg/ml, pH 3.77.

EXAMPLE 229

3α-Hydroxy-11β-4'-methylpiperidinoacetoxy-19-nor-5α-pregnan-20-one and its citrate salt Sodium iodide (0.330 g) and 4-methyl-piperidine (0.7 ml) were added to a solution of 11β-chloroacetoxy-3α-hydroxy-19-nor-5α-pregnan-20-one (0.330 g) in acetone (12 ml) and the mixture was left at room temperature for 43 hrs., then diluted with water to dissolve the precipitate. The solution was evaporated and the residue was partitioned between ethyl acetate and 2N hydrochloric acid (25 ml). The ethyl acetate solution was extracted twice more with 2N hydrochloric acid (25 ml) and the acid fractions were combined and basified with 2N sodium hydroxide solution. The precipitated steroid was extracted into ethyl acetate (twice) and the organic extracts were combined and washed with water until the washings remained at neutral pH. The ethyl acetate solution was dried over anhydrous sodium sulphate and evaporated to give a foam (0.354 g). This was crystallised from methanol/water giving the title compound as needles (0.256 g), m.p. 127°–129°, $[\alpha]_D + 101°$.

The above free base (115 mg) was added to a solution of citric acid monohydrate (52.5 mg) in water (2 ml). More water (8 ml) was added and finally the solution was made up to 11.5 g with water. This solution was filtered through a millipore filter yielding an anqueous solution of the title citrate, concentration 10 mg/ml, pH 3.73.

EXAMPLE 230

11β-Bis-N,N-(3-bromopropyl)aminoacetoxy-3α-hydroxy-5α-pregnan-20-one

11β-Aminoacetoxy-3α-hydroxy-5α-pregnan-20-one (1 g) was stirred under reflux with 1,3-dibromopropane (8 ml), potassium carbonate (2 g) and sodium iodide (0.4 g) in ethanol (20 ml) for 8 hours. The mixture was filtered and the filtrate was evaporated to dryness at reduced pressure. The residue was partitioned between ethyl acetate and sodium carbonate solution. The organic layer was washed with brine, dried (sodium sulphate) and evaporated to a gum which was purified by preparative TLC in ethyl acetate. The eluate of the main band was concentrated and crystallised from petrol to give the title compound (0.30 g), m.p. 87°–89°, $[\alpha]_D + 67.5°$.

The following preparations illustrate the preparation of intermediates required in the above Examples.

Preparation 1

20,20-Ethylenedioxy-5α-pregn-2-en-11-one

5α-Pregn-2-ene-11,20-dione (10 g) in benzene (300 ml) was treated with ethylene glycol (30 ml) and toluene-4-sulphonic acid (100 mg), and the vigorously stirred mixture was refluxed through a Dean and Stark separator for 8 hours. The reaction mixture was partitioned between ether/ethyl acetate and dilute sodium bicarbonate solution. The organic layer was washed with water (3 times), dried over sodium sulphate and evaporated to a solidifying oil which was triturated with petrol to give title compound (9.42 g) as an off-white solid, m.p. 130°–135°, $[\alpha]_D + 111°$.

Preparation 2

20,20-ethylenedioxy-3α-hydroxy-6β-methyl-5α-pregnan-11-one was prepared by the general method of Preparation 1. The product was purified by column chromatography and crystallisation from diethyl ether-petrol.

M.p. 112°–13°, $[\alpha]_D + 30.8°$.

Preparation 3

20,20-Ethylenedioxy-3α-hydroxy-16α-methyl-5α-pregnan-11-one

A mixture of 3α-hydroxy-16α-methyl-5α-pregnane-11,20-dione (1.00 g), benzene (50 ml), ethylene glycol (5 ml) and toluene-4-sulphonic acid monohydrate (50 mg) was brought to reflux under a Dean and Stark water separator and refluxed for 5 hr, then poured into saturated aqueous sodium hydrogen carbonate (50 ml) and the layers separated. The aqueous portion was extracted with additional benzene (50 ml) and the combined organic portions washed with water (2 × 50 ml), dried and evaporated to a white foam (1.12 g). A portion of this material (1.00 g) was crystallised from ether-petroleum ether (b.p. 60°–80°) to afford the title compound (581 mg), m.p. 122°–124°, $[\alpha]_D + 37.2°$.

Preparation 4

20,20-Ethylenedioxy-3α-hydroxy-21-methoxy-5α-pregnan-11-one was prepared by the general method of Preparation 3. (crystallised from methanol-pyridine (99:1)).

M.p. 188°–189°, $[\alpha]_D + 56°$.

PREPARATION 5

3,3:20,20-Bis-ethylenedioxy-5α-pregnan-11-one

5α-Pregnane-3,11,20-trione (5.0 g) in ethylene glycol (250 ml) was refluxed at 100°/20 mm. for one hour with toluene-p-sulphonic acid (0.1 g) under nitrogen. A second portion of toluene-p-sulphonic acid was then added and the suspension refluxed for a further five hours, poured into dilute aqueous sodium bicarbonate (1500 ml), and the precipitate (6.05 g) collected, washed and dried. Three crystallisations from methanol (with a drop of pyridine) gave the title compound m.p. 209°–211°, $[\alpha]_D + 48°$.

PREPARATION 6

20,20-Ethylenedioxy-5α-pregn-2-en-11β-ol 20,20-Ethylenedioxy-5α-pregn-2-en-11-one (9.3 g) in hot ethanol (300 ml) was treated with sodium borohydride (5.5 g) in water (30 ml), and the mixture was refluxed on a steam bath for 1 1/2 hours, concentrated by evaporation to about 200 ml, the excess borohydride destroyed by the addition of glacial acetic acid (0.5 ml), and the mixture poured on to ice-water to give a white crystalline precipitate. The precipitate was filtered off, washed with water and dried in vacuo to give title compound (9.05 g), as colourless needles, m.p. 141°–145°, $[\alpha]_D + 64°$.

By the general method of Preparation 6 the following compounds were prepared from their corresponding 11-ketones:

PREPARATION 7

20,20-Ethylenedioxy-2β-methyl-5α-pregnane-3α,11β-diol (Refluxed for 6 1/2 hours) m.p. 163°–167°, $[\alpha]_D + 43°$.

PREPARATION 8

17β-Cyano-5α-androstane-3α,11β-diol (Refluxed for 70 minutes).

The product was purified by extraction into ethyl acetate and crystallisation from ether-petrol.

M.p. 219°–221°.

PREPARATION 9

20,20-Ethylenedioxy-5α-pregnane-3α,11β-diol
(Refluxed for 2 hours).

The product was purified by extraction into ethyl acetate and trituration with petrol.

M.p. 189°–193°, $[\alpha]_D + 33.7°$.

PREPARATION 10

3α,11β-Dihydroxy-6β-methyl-5α-pregnan-20-one 20,20-Ethylenedioxy-3α-hydroxy-6β-methyl-5α-pregnan-11-one (1.36 g) was dissolved in propan-2-ol (90 ml) and a solution of sodium borohydride (500 mg) in water (10 ml) was added. The solution was stirred at 20° overnight and then diluted with water (200 ml). Extraction with chloroform (2×100 ml) gave, on evaporation of the extract, a colourless gum which was dissolved in a mixture of acetone (50 ml) and 2N-hydrochloric acid (5 ml). After 2 hours the solution was diluted with water (100 ml) and extracted with chloroform (2×50 ml). Evaporation of the extract gave a colourless gum which was crystallised from methanol (25 ml) to give the title compound (700 mg), m.p. 211°-213°.

PREPARATION 11

3α-11β-Dihydroxy-21-methoxy-5α-pregnan-20-one was prepared from 20,20-ethylene-dioxy-3α-hydroxy-21-methoxy-5α-pregan-11-one by the general method of Preparation 10.

m.p. 177°-179°, $[\alpha]_D$ +15°.

PREPARATION 12

20,20-Ethylenedioxy-2α-methyl-5α-pregnane-3α,11β-diol 20,20-Ethylenedioxy-3α-hydroxy-2α-methyl-5α-pregnan-11-one (3.0 g) was dissolved in propan-2-ol (150 ml) and sodium borohydride (1.0 g) in water (15 ml) was added. The solution was stirred overnight at 20° and then the excess sodium borohydride was decomposed by the addition of glacial acetic acid (0.3 ml). The mixture was diluted with water (100 ml) and extracted with chloroform (3×50 ml). The organic extract was washed with water (2×50 ml) and dried (MgSO$_4$). Evaporation of the solvent and crystallisation of the residue from ethyl acetate petrol gave the title compound (1.42 g), m.p. 157°-158°, $[\alpha]_D$ +46°.

PREPARATION 13

3,3;20,20-Bis-ethylenedioxy-5α-pregnan-11β-ol 3,3;20,20-Bis-ethylenedioxy-5α-pregnan-11-one (500 mg) in tetrahydrofuran (25 ml) was treated with a solution of sodium borohydride (200 mg) in water (5 ml). The reaction mixture was stirred at room temperature for 3 hours. The excess borohydride was destroyed by the addition of glacial acetic acid (5 drops), and the solution was diluted with ice-water. The crystalline precipitate was filtered off and dried to give title compound (500 mg), as fine white crystals, m.p. 160°-164°, $[\alpha]_D$+34°.

PREPARATION 14

20,20-Ethylenedioxy-16α-methyl-5α-pregnane-3α,11β-diol

A solution of sodium borohydride (4.12 g) in water (41 ml) was added to a refluxing solution of 20,20-ethylenedioxy-3α-hydroxy-16α-methyl-5α-pregnan-11-one (7.55 g) in ethanol (375 ml) containing pyridine (7 drops). The mixture was refluxed for 1 hr. then cooled and glacial acetic acid added until no further effervescence occurred. The mixture was partitioned between 3%-aqueous sodium hydrogen carbonate and ethyl acetate. The aqueous portion was extracted with additional ethyl acetate. The combined organic extracts were washed with saturated brine solution, dried and evaporated to a white foam which crystallised from acetone-water to afford the title compound as white prisms (3.29 g), m.p. 109°-111°, $[\alpha]_D$+17.0°.

PREPARATION 15

Methyl 3α,11β-dihydroxy-5α-androstane-17β-carboxylate

Sodium borohydride (1.24 g) in water (7 ml) was added to a solution of methyl 3α-hydroxy-11-oxo-5α-androstane-17β-carboxylate (2.58 g) in methanol (60 ml) and the mixture refluxed for 30 minutes. A further portion of sodium borohydride (200 mg) in a little water was added and refluxing continued for 10 minutes more. Most of the solvent was removed in vacuo and, after cooling, the crystalline product was collected by filtration. Recrystallization from aqueous methanol afforded title compound (1.662 g), m.p. 190°-197° with previous heavy sweating above 170°, $[\alpha]_D$ +66.7° (c 0.9).

PREPARATION 16

11β-Hydroxy-5α-pregnane-3,20-dione 3,3;20,20-Bis-ethylenedioxy-5α-pregnan-11β-ol (400 mg) in glacial acetic acid (10 ml) and water (10 ml) was stirred and heated at reflux for 2¼ hours. The solution was evaporated to dryness and the residue recrystallised from acetone/petrol to give title compound (215 mg) as colourless prisms, m.p. 227°-233° (with softening above 210°), $[\alpha]_D$ +115° (c 0.063%).

By a similar method to Preparation 16, but using the conditions indicated in Table 6, the following compounds were prepared from their 3α-hydroxy-20,20-ethylenedioxy analogues

PREPARATION 17

11β-Hydroxy-5α-pregn-2-en-20-one

PREPARATION 18

3α,11β-Dihydroxy-2β-methyl 5α-pregnan-20-one

PREPARATION 19

3α, 11β-Dihydroxy-5α-pregnan-20-one

PREPARATION 20

3α,11β-Dihydroxy-3β-methyl-5α-pregnan-20-one

PREPARATION 21

3α,11β-Dihydroxy-2α-methyl-5α-pregnan-20-one

PREPARATION 22

3α,11β-Dihydroxy-16α-methyl-5α-pregnan-20-one

TABLE 6

| Preparation No. | Acid | Solvent | Reaction Time (mins) | Reaction Temp. (°C.) | M.p. (°C.) | $[\alpha]_D$ |
|---|---|---|---|---|---|---|
| 17 | CH$_3$CO$_2$H | W | 90 | Reflux | 171-176 | +137° |
| 18 | PTSA | Ac | 60 | 20 | 198-200 | +32.8° |

TABLE 6-continued

| Preparation No. | Acid | Solvent | Reaction Time (mins) | Reaction Temp. (°C.) | M.p. (°C.) | $[\alpha]_D$ |
|---|---|---|---|---|---|---|
| 19 | PTSA | Ac | — | 20 | 205–207 | +100° |
| 20 | PTSA | Ac | 20 | 20 | 217–221 | +110.6° |
| 21 | HCl | Ac | 30 | 20 | 197–200 | +107° |
| 22 | PTSA | Ac | 60 | 21 | 180–182 | +84.0° |

PTSA = toluene-4-sulphonic acid;

The following work-up procedures were used:

PREPARATIONS 17 and 19

The reaction mixture was diluted with water and the precipitated solid collected.

PREPARATION 20

The reaction mixture was diluted with water, extracted into ethyl acetate, the extract washed, dried and evaporated and the product crystallised from ethyl acetate-petrol and aqueous acetone.

PREPARATION 18

Sodium bicarbonate solution was added to the reaction mixture which was concentrated and diluted with water. The precipitate was extracted into ether/ethyl acetate, purified by preparative TLC and triturated with ether.

PREPARATION 21

The reaction mixture was reduced in volume, diluted with 1% sodium bicarbonate solution and the precipitate collected.

PREPARATION 22

5% Sodium bicarbonate solution was added to the reaction mixture, which was evaporated and partitioned between water and ethyl acetate. The organic extracts were washed, dried and evaporated to yield a solid which was crystallised from ethyl acetate.

PREPARATION 23

11β-Chloroacetoxy-3α-hydroxy-5α-pregnan-20-one

Chloroiridic acid reagent (10 ml) was neutralised to pH7 with triethylamine (1.1 ml), and to it was added 11β-chloroacetoxy-5α-pregnane-3,20-dione (880 mg). The solution was refluxed for 4 hours, and then cooled and diluted with water. The oily precipitate was extracted into ether/ethyl acetate, and the organic layer was washed with water, dried over sodium sulphate and evaporated to a yellow foam (875 mg) which was purified by preparative TLC in ethyl acetate/petrol (1/1) to give title compound (750 mg) as a white foam, $[\alpha]_D$ +100° (c 0.62%).

By the general procedure of Preparation 23 the following compounds were prepared from their corresponding 3-ketones

PREPARATION 24

3α-Hydroxy-6β-methyl-5α-pregnane-11,20-dione. $[\alpha]_D$ +88°

PREPARATION 25

11β-Acryloyloxy-3α-hydroxy-5α-pregnan-20-one, m.p. 62°–70°, $[\alpha]_D$ +109°.

PREPARATION 26

11β-Chloroacetoxy-2α,3α-epoxy-5α-pregnan-20-one

11β-Chloroacetoxy-5α-pregn-2-en-20-one (1.25 g) in chloroform (50 ml) was treated with m-chloroperbenzoic acid (85%; 700 mg) and the solution was stirred at room temperature for 4 hours. Chloroform (50 ml) was added, and the solution was washed with potassium bicarbonate solution and with water; it was then dried over sodium sulphate and evaporated to a white foam which was triturated with ether to give title compound (1.05 g) as colourless prisms, m.p. 163°–169°, $[\alpha]_D$ +107°.

PREPARATION 27

2α,3α-Epoxy-11β-iodoacetoxy-5α-pregnan-20-one was prepared by the general method of Preparation 26. m.p. 117°–140°, $[\alpha]_D$ +85.5°.

PREPARATION 28

Methyl 3α,11β-bischloroacetoxy-5α-androstane-17β-carboxylate

A solution of methyl 3α,11β-dihydroxy-5α-androstane-17β-carboxylate (507 mg) in dioxan (15 ml) was treated with chloroacetic anhydride (1.21 g), pyridine, (0.6 ml) and 4-dimethylaminopyridine (42 mg) and the mixture was kept at room temperature. After 4.5 hours water was added, most of the solvent was removed in vacuo and the residue was partitioned between water and ethyl acetate. The organic extract was washed with dilute hydrochloric acid, water, sodium bicarbonate and water and evaporated to afford an oil. Purification by preparative t.l.c. using 2% methanol in chloroform gave an oil which was crystallized with ether-petroleum ether to yield title compound (507 mg), m.p. 149°–155°, $[\alpha]_D$ +86.6° (c 0.4).

By the general method of Preparation 28 the following compound were prepared from their corresponding 3α,11β-diols:

PREPARATION 29

3α,11β-Bischloroacetoxy-5α-pregnan-20-one Reaction time 1 hour, more 4-dimethylamino-pyridine was added after 30 minutes. M.p. 117°–119°, $[\alpha]_D$ +114.2° (c 0.16).

PREPARATION 30

3α,11β-Bischloroacetoxy-21-methoxy-5α-pregnan-20-one.

Reaction time 4 hours. The reaction mixture was diluted with 5% sodium bicarbonate solution and extracted with ethyl acetate to yield the title compound after evaporation of the extract.

PREPARATION 31

3α,11β-Bischloroacetoxy-16α-methyl-5α-pregnan-20-one

Reaction time 6 hours. The reaction mixture was worked-up as in Preparation 30. The product was purified by chromatography on silica gel and crystallised from ether-petrol.

M.p. 138.5°-140.5°, $[\alpha]_D$ +91.0°.

PREPARATION 32

3α,11β-Bischloroacetoxy-6β-methyl-5α-pregnan-20-one

Reaction time 2 hours. The reaction mixture was worked-up as in Preparation 30. The product was crystallised from ether-petrol.

M.p. 134°-135°, $[\alpha]_D$ +92°.

PREPARATION 33

3α,11β-Bischloroacetoxy-20,20-ethylenedioxy-5α-pregnane

Reaction time 18 hours. The reaction mixture was diluted with ethyl acetate, washed with sodium bicarbonate solution, dried and evaporated. The residue was purified by column chromatography, preparative TLC and crystallisation.

M.p 113°-117°, $[\alpha]_D$ +62.6° (c 0.26).

PREPARATION 34

3α,11β-Bischloroacetoxy-2α-methyl-5α-pregnan-20-one

Reaction time 4 hours. The reaction mixture was worked-up as in Preparation 30. The product was crystallised from ethyl acetate-petrol.

M.p. 132°-134°, $[\alpha]_D$ +142.8°.

PREPARATION 35

3β,11β-Bischloroacetoxy-5α-pregn-16-en-20-one

Reaction time 23 hours. The reaction mixture was worked-up as in Preparation 30.

PREPARATION 36

3α,11β-Bischloroacetoxy-3β-methyl-5α-pregnan-20-one

Reaction time 3 hours. The reaction mixture was worked up as in Preparation 30. The product was purified by chromatography and crystallisation from ether-petrol.

M.p. 118°-121°, $[\alpha]_D$ +109.3°.

In Preparations 30-32 and 34-36 no pyridine was used.

In Preparations 35 and 36 calcium carbonate was present in the reaction mixture, and the reaction mixture was filtered prior to work-up.

PREPARATION 37

3α,11β-Bischloroacetoxy-2β-methyl-5α-pregnan-20-one

3α,11β-Dihydroxy-2β-methyl-5α-pregnan-20-one (250 mg) was mixed with chloroacetic anhydride (500 mg) in dioxan (10 ml) containing 4-dimethylaminopyridine (25 mg). After 5 hours, further chloroacetic anhydride (200 mg) was added and reaction appeared complete by tlc after 23 hours. Excess sodium hydrogen carbonate solution was added until pH8 was reached and maintained during stirring for 20 minutes to hydrolyse remaining chloroacetic anhydride. The mixture was extracted with ethyl acetate (three times) and the combined organic solutions were washed with brine (twice), dried with magnesium sulphate and evaporated to a gum (493 mg). Attempted crystallisation from methanol-water gave title compound (253 mg). $[\alpha]_D$ +117°.

PREPARATION 38

3α,11β-Bis-2'-Bromopropionyloxy-5α-pregnan-20-one

A mixture of 3α,11β-dihydroxy-5α-pregnan-20-one (1 g), 4-dimethylaminopyridine (50 mg), calcium carbonate (2 g) and 2-bromopropionic anhydride (2 ml) in dioxan (50 ml) was stirred at room temperature for about 20 hours. A further portion (200 mg) of 4-dimethylaminopyridine was added and after another 2 hours stirring the mixture was heated to 60°. More 4-dimethylaminopyridine (500 mg) was added after 3 hours and 18 hours later more 2-bromopropionic anhydride (2 ml) was added and the mixture was then kept for 3 days at room temperature. Solid material was removed by filtration and the filtrate was diluted with water and extracted with ethyl acetate. Evaporation of the organic extract gave a froth which was purified by preparation t.l.c. and crystallization from ether-petroleum ether to afford title compound m.p. 143°-158° $[\alpha]_D$ +86° (110 mg).

PREPARATION 39

3α,11β-Bis-2'-chloropropionyloxy-20,20-ethylenedioxy-5α-pregnane

A mixture of 20,20-ethylenedioxy-5α-pregnane-3α,11β-diol (1 g), 2-chloropropionic anhydride (2 ml) and 4-dimethylaminopyridine (50 mg) in dioxan (25 ml) containing pyridine (1.2 ml) was stirred at 85° for about 24 hours, more 4-dimethylaminopyridine (100 mg) being added after 1.5 and 20 hours. After a further 3.5 hours more 2'-chloropropionic anhydride (0.5 ml) was added and the mixture was heated to reflux for 1 hour, cooled, partitioned between water and ethyl acetate and the organic extract was washed, dried and evaporated in vacuo. The residue was purified by preparative t.l.c. and crystallization from ether-petroleum ether to give title compound, m.p. 152°-158°, $[\alpha]_D$ +48.6° (320 mg).

PREPARATIONS 40-47

Table 7 summarises the preparation of the following compounds:

40. 11β-(N-Butyl-N-methylaminoacetoxy)-2α,3α-epoxy-5α-pregnan-20-one
41. 11β-Dipropylaminoacetoxy-5α-pregnane-3,20-dione
42. 3α,11β-Bis-N,N-dipropylaminoacetoxy-5α-pregnan-20-one
43. 20,20-Ethylenedioxy-11β-dipropylaminoacetoxy-5α-pregnan-3α-ol
44. 2α,3α-Epoxy-11β-4'-methylpiperidinoacetoxy-5α-pregnan-20-one
45. 11β-Diethylaminoacetoxy-2α,3α-epoxy-5α-pregnan-20-one
46. 11β-Aminoacetoxy-3α-hydroxy-5α-pregnan-20-one
47. 11β-Dipropylaminoacetoxy-3β-hydroxy-5α-pregn-16-en-20-one The corresponding 11β- iodo acetate in the solvent indicated was treated with the appropriate amine for the specified time and evaporated in vacuo. The residue was then worked-up by one of the methods A-C described in Examples 4–73. In some cases the product was purified by preparative TLC and/or crystallization.

added dropwise with good stirring to a cooled (−5°) solution of methanesulphonyl chloride (3.77 ml) in methylene chloride (50 ml) at such a rate that the temperature did not exceed +1°. After 30 minutes a further portion of methanesulphonyl chloride (3 ml) and trieth-

TABLE 7

| Preparation No. | Iodo-acetate (g) | Amine (ml) | Solvent | Vol. (ml) | Reaction time (hrs) | Crystal-lisation solvent | Yield (g) | M.P. (C) | $[\alpha_D]$ | Method of work-up |
|---|---|---|---|---|---|---|---|---|---|---|
| 40 | 3 | 6 | DC | 100 | 3 | — | 2.62 | — | — | C [1] |
| 41 | .400 | 1 | MC | 10 | 24 | — | .300 | 98–101 | +103° | C |
| 42[2] | 1.7 | 6 | DC | 100 | 4 | — | 1.55 | — | +81.0° | C |
| 43 | .500 | 1 | MC | 10 | 24 | EA-PE | .190 | 129–130 | +40° | A |
| 44 | 1.9 | 2 | MC | 50 | ½ | Ac-PE | 1.52 | 141–145 | +97.5° | C |
| 45 | 2.6 | 8 | MC | 50 | 2½ | M-W | 1.88 | 77–79 | +103° | C |
| 46 | .500 | 3[3] | D | 15 | 1 | — | .226 | — | +104° | B |
| 47 | .675 | 1.5 | DC | 25 | 48 | PE | .361 | 100–102 | +51.6° | A |

[1]The residue was dissolved in methanol, diluted with water and the precipitate collected.
[2]The 3α,11β-bisiodoacetate was used as starting material.
[3]k80 Ammonia solution.

PREPARATION 48

20,20-Ethylenedioxy-3α-hydroxy-2β-methyl-5α-pregnan-11-one

A stirred suspension of dried cuprous iodide (19.6 g) in dry xylene (350 ml) under nitrogen was cooled to −10° and 1.9 M methyl lithium in ether (108 ml) was added until the initial yellow precipitate redissolved to give an almost clear colourless solution. A solution of 20,20-ethylenedioxy-2α,3α-epoxy-5α-pregnan-11-one (12.9 g) in xylene (430 ml) was added dropwise at −10° to −5°. After the addition, the mixture was stirred overnight at room temperature, and then poured into 25% ammonium chloride solution (1200 ml). The mixture was extracted with ether (1200 ml) and the extract was washed with 25% ammonium chloride solution (1200 ml) and water (1200 ml). Evaporation of the ether left an oily solid which from tlc on silica was a 2:1 mixture of the starting material and the title compound. This solid was recycled using the same quantities of reagents, temperatures and times. The resulting solid was crystallised from ethyl acetate-petroleum ether (b.p. 60°–80°) to give the title compound (7.22 g), m.p. 167°–168°, $[\alpha]_D$ +68.1°.

PREPARATION 49

3α-4′-Chlorobutyryloxy-11β-hydroxy-5α-pregnan-20-one

A solution of 3α,11β-dihydroxy-5α-pregnan-20-one (1.552 g) in dioxan (65 ml) was treated with chlorobutyric anhydride (6.392 g), calcium carbonate (6.37 g) and dimethylaminopyridine (103 mg) and the mixture stirred at room temperature for 22 hours. Excess dilute hydrochloric acid was added and after several hours the organic products were extracted into ethyl acetate. The washed extract was evaporated to give an oily solid which was triturated with petroleum ether containing just sufficient ether to give a free flowing solid which was collected by filtration and recrystallized from aqueous methanol to yield title compound (1.485 g), m.p. 155°–158°.

PREPARATION 50

11β-Iodoacetoxy-3α-methanesulphonyloxy-5α-pregnan-20-one

A solution of 3α-hydroxy-11β-iodoacetoxy-5α-pregnan-20-one (20 g) in methylene chloride (400 ml) containing triethylamine (8.4 ml) was cooled to −5° and ylamine (6 ml) was added in a small volume of methylene chloride. After 10 minutes the solution was washed with water, dried and evaporated to give a yellow solid (22.43 g). Crystallization of a small portion afforded an analytical sample of title compound, m.p. 142°–143°, $[\alpha]_D$ +83.2°.

PREPARATION 51

11β-Iodoacetoxy-5α-pregn-2-en-20-one

A solution of 11β-iodoacetoxy-3α-methanesulphonyloxy-5α-pregnan-20-one (22.2 g) in t-butanol (950 ml) containing water (500 ml) was treated with powdered silica gel (44 g) and refluxed with stirring for 75 minutes. The cooled mixture was filtered and the filtrate was evaporated to small bulk and diluted with water. The precipitated solid was collected by filtration and recrystallized from aqueous methanol to afford title compound (12.77 g). A sample recrystallized from acetone-petroleum ether had m.p. 127°–129°, $[\alpha]_D$ +100.5°.

PREPARATION 52

3α-Acetoxy-17β-cyano-5α-androstan-11β-ol

A solution of 17β-cyano-5α-androstane-3α,11β-diol (20 mg) in acetic anhydride (0.5 ml) containing pyridine (0.5 ml) was kept at room temperature for three days. The mixture was diluted with 2N-hydrochloric acid and extracted with ethyl acetate. Evaporation of the organic extract afforded title compound (21 mg).

PREPARATION 53

6β-Methyl-5α-pregnane-3,11,20-trione

6-Methylpregna-4,6-diene-3,11,20-trione (1.7 g) in ethyl acetate (100 ml) was hydrogenated at atmospheric pressure using 10% palladium on charcoal (500 mg) as catalyst. The catalyst was filtered off and the filtrate evaporated. Crystallisation of the residue from acetonepetroleum ether (b.p. 60°–80°) gave the title compound (720 mg), m.p. 174°–176°, $[\alpha]_D$ +106°.

PREPARATION 54

11β-N,N-Dipropylaminoacetoxy-3β-hydroxy-5α-pregnan-20-one

11β-N,N-Dipropylaminoacetoxy-3β-hydroxy-5α-pregn-16-en-20-one (150 mg) was stirred with 5% palladium on charcoal (100 mg) in ethyl acetate (25 ml) at 20° under hydrogen. After 1 hour the catalyst was separated off using a Kieselguhr filter aid and the ethyl acetate was evaporated to leave a white solid. This was recrystallised from ethyl acetate in petroleum ether to give title compound as white crystals, m.p. 145 to 147.5 [α]$_D$ +85.2°. (89 mg).

PREPARATION 55

2β-Acetoxy-11β-chloroacetoxy-3α-hydroxy-5α-pregnan-20-one

11β-Chloroacetoxy-2α,3α-epoxy-5α-pregnan-20-one (5 g) was dissolved in glacial acetic acid (25 ml) and heated on a steam bath for 3.¼ hrs. The solution was poured into saturated sodium bicarbonate solution, the white precipitate filtered off, washed well with water and dried. Preparation thick layer chromatography in ethyl acetate-petrol gave the title compound as a white foam (3.26 g). [α]$_D$ +93.2°.

PREPARATION 56–60

Preparation of 2β-alkoxy-11β-chloroacetoxy-3α-hydroxy-5α-pregnan-20-ones

Table 8 summarises the preparation of the title compounds by the following method:

11β-Chloroacetoxy-2α,3α-epoxy-5α-pregnan-20-one (10 parts) was dissolved in the appropriate dry alcohol (100 parts by vol.) and concentrated sulphuric acid (0.1 parts) or boron trifluoride diethyl etherate (1 part) added. After the time indicated, the reaction mixture was poured into saturated sodium bicarbonate solution and the product isolated by either of the following methods:

A. The precipitate was filtered off, washed and dried.
B. The product was extracted into (i) ether or (ii) ethyl acetate. The organic phase was washed, dried, filtered and evaporated.

The products from either of those methods were purified by column chromatography over silica (ethylacetate-petrol) and/or crystallisation.

PREPARATION 62

11β-Chloroacetoxy-5α-pregn-2-en-20-one

A mixture of 11β-hydroxy-5α-pregn-2-en-20-one (8.7 g), calcium carbonate (11 g) and chloroacetic anhydride (13.85 g) in dioxan (260 ml) containing pyridine (8.7 ml) and 4-dimethylaminopyridine (348 mg) was stirred at room temperature for 18 hours. The mixture was poured into 2N-hydrochloric acid and extracted into ethyl acetate. The washed and dried extract was evaporated in vacuo and the oily residue was crystallised from ether and then ethyl acetate-petroleum ether to afford the title compound, m.p. 145°–147°, [α]$_D$ +123.6° (8.7 g).

PREPARATION 63

3α,11β-Bis-4′-chlorobutyryloxy-5α-pregnan-20-one

3α-4′-Chlorobutyryloxy-11β-hydroxy-5α-pregnan-20-one (1.306 g) in dioxan (25 ml) was treated with calcium carbonate (3.307 g), chlorobutyric anhydride (3.22 g) and 4-dimethylaminopyridine (110 mg). The mixture was stirred at room temperature for 3 days and then at 80° for 20 hours. The mixture was diluted with hydrochloric acid, extracted into ethyl acetate and washed thoroughly with hydrochloric acid, sodium bicarbonate and water. Evaporation afforded an oil which was separated into two components by preparative t.l.c., the less polar major fraction giving title compound as an oil (1.084 g).

PREPARATION 64

3α-Acetoxy-11β-chloroacetoxy-5α-androstane-17β-carbonitrile

A solution of 3α-acetoxy-11β-hydroxy-5α-androstane-17β-carbonitrile (250 mg) in dioxan (10 ml) was treated with 4-dimethylaminopyridine (25 mg) and chloroacetic anhydride (500 mg). The mixture was kept at room temperature for 20 minutes and was then diluted with sodium bicarbonate solution, allowed to stand for 10 minutes and then extracted into ethyl acetate. Evaporation of extract and crystallization of the residue from ether-petroleum ether afforded title compound, m.p. 187°–190°, (144 mg).

TABLE 8

| Preparation | 2β-substituent | catalyst | 2α, 3α-Epoxide (g) | crystallisation solvent | Reaction Time (hrs.) | Yield (g) | M.P. (°C.) | [α]$_D$ | Method of work-up |
|---|---|---|---|---|---|---|---|---|---|
| 56 | —OCH$_3$ | conc. H$_2$SO$_4$ | 20 | DE | ½ | 13.3 | 134–140 | +101° | A |
| 57 | —OC$_2$H$_5$ | conc. H$_2$SO$_4$ | 15 | EA-PE | 1 | 5 | 103–110 | +90° | B(ii) |
| 58 | —OC$_3$H$_7$ | conc. H$_2$SO$_4$ | 10 | — | 1 | 6 | — | +84.5° | B (i) |
| 59 | —OCH(CH$_3$)$_2$ | BF$_3$ . E$_2$O | 9 | M-W | 3.5 | 5.1 | 130–135 | +95.5° | B (ii) |
| 60 | —OC$_4$H$_9$ | BF$_3$ . E$_2$O | 10 | DE | 2.5 | 4.1 | 155–158 | +89.7° | B (i) |

PREPARATION 61

11β-Chloroacetoxy-5α-pregnane-3,20-dione

11β-Hydroxy-5α-pregnane-3,20-dione (2 g) was stirred with chloroacetic anhydride (6.5 g) and calcium carbonate (10 g) is dioxan (200 ml.) containing 4-dimethylaminopyridine (450 mg, added in 2 portions) at 20° for 3 hours. The reaction mixture was filtered and the filtrate was adjusted to pH8 by addition of sodium hydrogen carbonate solution. The crystalline precipitate was collected by filtration, washed, and dried to give title compound (2 g), m.p. 133°–135°, [α]$_D$ +113°.

PREPARATION 65

2β-Ethoxy-3α-hydroxy-11β-iodoacetoxy-5α-pregnan-20-one

11β-Chloroacetoxy-2β-ethoxy-3α-hydroxy-5α-pregnan-20-one (420 mg) in acetone (42 ml) was treated with sodium iodide (550 mg) and the solution was refluxed for one hour, during which time a fine white precipitate formed. The filtered solution was evaporated to an oily solid which was partitioned between ether/ethyl acetate and water. The organic layer was washed with water, dried over sodium sulphate and evaporated to give title compound (510 mg) as a white form, $[\alpha]_D$ +80° (c 0.32%).

By the general method of Preparation 65 the following compounds were prepared from the corresponding 11β-chloroacetates:

PREPARATION 66

3α-Hydroxy-11β-iodoacetoxy-5α-pregnan-20-one
m.p. 116°-119°, $[\alpha]_D$ +82.2°.

PREPARATION 67

3α-Hydroxy-11β-iodoacetoxy-2β-methyl-5α-pregnan-20-one
M.p. 132°-134°, $[\alpha]_D$ +93° (c, 0.64).

PREPARATION 68

3α-Hydroxy-11β-iodoacetoxy-2β-methoxy-5α-pregnan-20-one m.p. 139°, $[\alpha]_D$ +82.8°.

PREPARATION 69

3α-Acetoxy-11β-iodoacetoxy-5α-androstane-17β-carbonitrile
M.p. 133°-136°, $[\alpha]_D$ +56°.

PREPARATION 70

3α-Hydroxy-11β-iodoacetoxy-3β-methyl-5α-pregnan-20-one
M.p. 128°-136°, $[\alpha]_D$ +83.5°.

PREPARATION 71

Methyl 3α-hydroxy-11β-iodoacetoxy-5α-androstane-17β-carboxylate
M.p. 104°-109°, $[\alpha]_D$ +48.5°.

PREPARATION 72

20,20-Ethylenedioxy-11β-iodoacetoxy-5α-pregnan-3α-ol
M.p. 174°-180°, $[\alpha]_D$ +32° (c, 0.14).

PREPARATION 73

11β-Iodoacetoxy-5α-pregnane-3,20-dione
M.p. 135°-136°, $[\alpha]_D$ +94°

In Preparations 70-73 the product was isolated by evaporation of the solvent, addition of water to the residue and collection of the precipitate by filtration.

PREPARATION 74

3α,11β-Bisiodoacetoxy-5α-pregnan-20-one

The title compound was prepared from the corresponding 3α,11β-bischloroacetate and the product was isolated by dilution with water of the filtered reaction mixture, extraction into ethylacetate of the precipitate and evaporation of the extract. The product was purified by column chromatography and crystallisation from ether,
M.p. 112°-113°, $[\alpha]_D$ +80.5°.

PREPARATION 75

3β-Hydroxy-11β-iodoacetoxy-5α-pregn-16-en-20-one.

The residue obtained by evaporation of the solvent was filtered through silica gel in ethyl acetate. The eluate was evaporated and the residue crystallised from ether-petrol to give the title compound,
M.p. 130°-131°, $[\alpha]_D$ +45°.

PREPARATION 76

11β-Chloroacetoxy-20,20-ethylenedioxy-5α-pregnan-3α-ol

A solution of 3α,11β-bischloroacetoxy-20,20-ethylenedioxy-5α-pregnane (1 g) in refluxing methanol was stirred whilst a saturated solution of sodium bicarbonate (2.5 ml) was added. The mixture was refluxed until reaction was judged complete (by t.l.c), most of the solvent was evaporated in vacuo and water was added. The crude product was collected by filtration and purified by preparative t.l.c. (ethyl acetate-petroleum ether 1:1) and crystallization from ethyl acetate-petroleum ether to give title compound m.p. 194°-202°, $[\alpha]_D$ +44° (c 0.1).

By the general method of Preparation 76 the following compounds were prepared from the corresponding 3α-chloroesters:

PREPARATION 77

11β-4'-chlorobutyryloxy-3α-hydroxy-5α-pregnan-20-one.

Crystallised from aqueous methanol,
M.p. 148°-154°.

PREPARATION 78

11β-chloroacetoxy-3α-hydroxy-21-methoxy-5α-pregnan-20-one
M.p. 67°-69°, $[\alpha]_D$ +93.1°.

PREPARATION 79

11β-Chloroacetoxy-3α-hydroxy-2α-methyl-5α-pregnan-20-one.

Crystallised from ethyl acetatepetrol,
M.p. 168°-172°, $[\alpha]_D$ +116.2°.

PREPARATION 80

11β-Chloroacetoxy-3α-hydroxy-6β-methyl-5α-pregnan-20-one.

M.p. 87°-89°, $[\alpha]_D$ +86.6°.

PREPARATION 81

Methyl 11β-chloroacetoxy-3α-hydroxy-5α-androstane-17β-carboxylate.

Crystallised from aqueous methanol,
M.p. 165°-167°, $[\alpha]_D$ +69.0°.

PREPARATION 82

11β-Chloroacetoxy-3α-hydroxy-2β-methyl-5α-pregnan-20-one.

m.p. 145°-147°, $[\alpha]_D$ +113°.

PREPARATION 83

11β-Chloroacetoxy-3α-hydroxy-3β-methyl-5α-pregnan-20-one.

Crystallised from ethyl acetate-petrol,
M.p. 164°-167°, $[\alpha]_D$ +107.5°.

PREPARATION 84

11β-Chloroacetoxy-3α-hydroxy-16α-methyl-5α-pregnan-20-one.

Crystallised from ether-petrol,
M.p. 167°-170°, $[\alpha]_D$ +87.9°.

PREPARATION 85

11β-2′-Bromopropionyloxy-3α-hydroxy-5α-pregnan-20-one.

Crystallised from ethyl acetate-petrol,
M.p. 149°-156°, $[\alpha]_D$ +90.4°.

In Preparations 83-85 the reaction mixture was diluted with water and extracted with ethyl acetate. The extract was washed, dried and evaporated to yield the product which was purified by preparation TLC and-/or crystallisation.

In Preparation 82 the reaction mixture was diluted with water and the precipitate collected by filtration and crystallised from ethyl acetate-petrol.

PREPARATION 86

11β-2′-Chloropropionyloxy-3α-hydroxy-5α-pregnan-20-one

A solution of 3α,11β-bis-2′-chloropropionyloxy-20,20-ethylenedioxy-5α-pregnane (7.86 g) in methanol (500 ml) was refluxed and stirred with saturated sodium bicarbonate solution (50 ml) for 4 hours. The cooled mixture was diluted with water and the precipitated solid was collected by filtration, washed with water and dried. This material was dissolved in acetone (200 ml) and treated with toluene-4-sulphonic acid (500 mg). After about 30 minutes water was added and the precipitate extracted into ether. Evaporation of the washed and dried extract afforded title compound (5 g) as a froth. A crystalline sample had m.p. 128°-139°, $[\alpha]_D$ +97.4° (c 0.14).

PREPARATION 87

11β-Chloroacetoxy-3β-hydroxy-5α-pregn-16-en-20-one

3β,11β-Bischloroacetoxy-5α-pregn-16-en-20-one (1.2 g) was stirred at 100° in dioxan (20 ml) containing water (4 ml) with sodium bicarbonate (1.26 g) for 4 hours. The mixture was cooled, poured into water and the precipitate collected by filtration, dried and filtered through silica gel (20 g) in ethylacetate. The eluate was evaporated and the residue crystallised from petrol containing a little ethyl acetate to yield the title compound (684 mg), m.p. 160.5°-162°, $[\alpha]_D$ +75.2°.

PREPARATION 88

11β-Acryloyloxy-5α-pregnane-3,20-dione

A mixture of 11β-hydroxy-5α-pregnane-3,20-dione (332 mg), dry dioxan (20 ml), 4-dimethylaminopyridine (33 mg) and acrylic anhydride (1 ml) was stood at room temperature overnight. More 4-dimethylaminopyridine (20 mg) was added and the mixture stood at room temperature for a further 5 days. The reaction mixture was kept at 100° for 48 hours before adding more 4-dimethylaminopyridine (100 mg) and acrylic anhydride (1 ml). After a further 72 hours at 100°, the reaction mixture was partitioned between ethyl acetate and saturated aqueous sodium bicarbonate solution. The organic phase was washed three times with water, dried ($Na_2SO_4$) and evaporated to a froth. Preparative TLC (ethyl acetate/petrol 1:1) and trituration with ether afforded title compound (60 mg). m.p. 135°-144°, $[\alpha]_D$ +122°.

PREPARATION 89

2β-Ethoxy-20,20-ethylenedioxy-3α-hydroxy-D-homo-5α-pregnan-11-one was prepared by the general method of Preparation 3. Purified by preparative TLC (ethylacetatepetrol) and crystallisation from ether-petrol, m.p. 140°-140°, $[\alpha]_D$ +8.4°.

PREPARATION 90

2β-Ethoxy-20,20-ethylenedioxy-D-homo-5α-pregnane-3α,11β-diol

A refluxing solution of 2β-ethoxy-20,20-ethylenedioxy-3α-hydroxy-D-homo-5α-pregnan-11-one (1.694 g) in industrial methylated spirits (40 ml) was treated with a solution of sodium borohydride (0.847 g) in water (7 ml). The mixture was refluxed for 1¼ hrs then cooled and treated with glacial acetic acid dropwise until no more effervescence occurred whereupon an oil was deposited. The mother liquors were decanted and upon standing colourless needles crystallised out and were collected by filtration (0.995 g). A sample (0.150 g) was recrystallised twice from ethanol/water yielding the title compound as colourless needles (0.020 g), m.p. 180°-7°, $[\alpha]_D$ +9.25°.

PREPARATION 91

3α,11β-Dihydroxy-2β-ethoxy-D-homo-5α-pregnan-20-one p-Toluene sulphonic acid monohydrate (0.092 g) was added to a refluxing solution of 2β-ethoxy-20,20-ethylenedioxy-D-homo-5α-pregnane-3α-11β-diol (0.920 g) in acetone (92 ml). After 15 minutes the reaction mixture was evaporated to low volume and the residue was partitioned between ethyl acetate and sodium bicarbonate solution. The ethyl acetate extract was washed with water, dried (anhydrous sodium sulphate) and evaporated to give the title compound as a white foam (0.831 g), $[\alpha]_D$ +61.0°.

PREPARATION 92

3α,11β-Bischloroacetoxy-2β-ethoxy-D-homo-5α-pregnan-20-one

A solution of 3α,11β-dihydroxy-2β-ethoxy-D-homo-5α-pregnan-20-one (0.780 g) in dry dioxan (20 ml) was treated with chloroacetic anhydride (1.65 g) and dimethylaminopyridine (0.100 g) at room temperature for 1 hour. Most of the dioxan was evaporated off and yellow oil partitioned between ethyl acetate and 2N hydrochloric acid. The ethyl acetate solution was washed with saturated sodium bicarbonate solution then water and dried over anhydrous sodium sulphate. Evaporation of the solution gave an oil which was crystallised from ethyl acetate/petrol to give the title compound as white needles (0.631 g), m.p. 127°-9°.

PREPARATION 93

11β-Chloroacetoxy-2β-ethoxy-3α-hydroxy-D-homo-5α-pregnan-20-one

A solution of sodium bicarbonate (0.060 g) in water (1.2 ml) was added to a solution of 3α,11β-bis-chloroacetoxy-2β-ethoxy-D-homo-5α-pregnan-20-one (0.100 g) in methanol (7 ml) and the mixture was refluxed for 20 minutes. Some of the methanol was evaporated off and the residue was partitioned between ethyl acetate and water. The ethyl acetate extract was washed with water, dried over anhydrous sodium sulphate and evaporated to yield the title compound as a white foam (0.090 g), $[\alpha]_D$ +56.5°.

PREPARATION 94

3β,11β-Dihydroxy-5α-pregn-16-en-20-one

3β-Hydroxy-5α-pregn-16-ene-11,20-dione (3 g) was refluxed with ethylene glycol (8 ml) in benzene (150 ml) containing p-toluenesulphonic acid (150 mg) under a Dean Stark water separator for 20 hours. The mixture was diluted with ethyl acetate, washed with sodium hydrogen carbonate solution, and brine, and dried (sodium sulphate). Evaporation gave 20,20-ethylenedioxy-3β-hydroxy-5α-pregn-16-en-11-one (3.42 g) as a white foam. This foam was dissolved in ethanol (170 ml) and sodium borohydride (2.1 g) in water (21 ml) was added with stirring under reflux. After 1.25 hours, most of the ethanol was evaporated and the residue was partitioned between ethyl acetate and water. The ethyl acetate extract was washed, and evaporated to small volume. This solution was filtered through silica gel (100 g) in ethyl acetate. Evaporation of the eluate gave 20,20-ethylenedioxy-5α-pregn-16-ene-3β,11β-diol (2.45 g) as a white foam which was heated on a steam bath for 1 hour in acetic acid (24 ml) and water (25 ml). The mixture was concentrated and diluted with water. The solid was collected by filtration, washed, and dried. Recrystallisation from ethyl acetate-acetone gave title compound (97 mg), m.p. 214°-218°, $[\alpha]_D$ +82.1°.

PREPARATION 95

20,20-Ethylenedioxy-2α,3α-epoxy-5α-pregnan-11-one

85%-m-Chloroperoxybenzoic acid (14.74 g) was added to a stirred solution of 20,20-ethylenedioxy-5α-pregn-2-en-11-one (26.0 g) at 20° to 25° during 15 minutes. After 45 minutes the solution was washed with 5% sodium hydrogen carbonate solution (2×300 ml) and water (300 ml). Evaporation of the solvent and crystallisation of the residue from 1% pyridine in methanol (300 ml) gave the title compound (23.6 g) m.p. 159°-160°.

PREPARATION 96

11β-Chloroacetoxy-3α-hydroxy-5α-pregnan-20-one

Saturated sodium bicarbonate solution (200 ml) was added slowly to a stirred refluxing solution of 3α,11β-bischloroacetoxy-5α-pregnan-20-one (89 g) in methanol (1800 ml). After about 3.5 hours the mixture was evaporated to half its volume, water was added and the steroid was extracted with ethyl acetate. The washed and dried extract was evaporated in vacuo, the residue was filtered through a short column of silica in ethyl acetate-petroleum ether (1:1) and crystallised from ethyl acetate-petroleum ether to afford title compound (59 g), m.p. 83°-86°, $[\alpha]_D$ +101° (c 1.0).

PREPARATION 97

20,20-Ethylenedioxy-3α-hydroxy-19-nor-5α-pregnan-11-one

3α-Hydroxy-19-nor-5α-pregnane-11,20-dione (7.95 g. 2.5 mmol) was dissolved in a mixture of chloroform (100 ml), ethylene glycol (23 ml) and triethyl orthoformate (14 ml). Toluene-4-sulphonic acid (300 mg) was added and the resulting clear solution was stirred at 20° for 2 hrs. The solution was then washed with 5% sodium hydrogen carbonate solution (100 ml), and water (100 ml), dried (MgSO₄) and evaporated to give a colourless gum (8.1 g). Crystallisation from ethyl acetate (30 ml) gave the title compound (5.29 g, 72.7%), m.p. 178°-179°, $[\alpha]_D^{21}$ +113° (c=1.22).

PREPARATION 98

20,20-Ethylenedioxy-19-nor-5α-pregnane-3α,11β-diol

A solution of 20,20-ethylenedioxy-3α-hydroxy-19-nor-5α-pregnan-11-one (2.0 g) in ethanol (50 ml) was treated with a solution of sodium borohydride (1.0 g) in water (8 ml) and the mixture was refluxed for 1 hr. The mixture was cooled and treated dropwise with glacial acetic acid until no more effervescence occurred. During this procedure a sticky oil was precipitated. The mother liquors were decanted, the oil was washed with ethanol and the washings combined with the mother liquors.

The mother liquors were diluted with water until crystallisation occurred. The title compound (1.168 g) was obtained as fine white needles, m.p. 214°-215°, $[\alpha]_D$ +50°.

PREPARATION 99

3α,11β-Dihydroxy-19-nor-5α-pregnan-20-one p-Toluene sulphonic acid monohydrate (0.170 g) was added to a solution of 20,20-ethylenedioxy-19-nor-5α-pregnane-3α,11β-diol (1.69 g) in acetone (150 ml) and the mixture was refluxed for 70 mins. The reaction mixture was concentrated to 50 ml under vacuum and then diluted with a large volume of water (~200 ml). The bulky white precipitate (1.372 g) was filtered off and washed with water. A portion (0.100 g) was crystallised from ethyl acetate/petrol yielding the title compound (0.061 g), m.p. 175°-190°, $[\alpha]_D$ +123.5°.

PREPARATION 100

11β-Chloroacetoxy-3α-hydroxy-19-nor-5α-pregnan-20-one

Chloroacetic anhydride (3.3 g) and dimethylaminopyridine (0.200 g) were added to a solution of 3α,11β-dihydroxy-19-nor-5α-pregnan-20-one (1.27 g) in dry dioxan (40 ml). After 25 mins. the reaction mixture was evaporated in vacuo to a yellow oil which was partitioned between ethyl acetate and 2 N hydrochloric acid. The ethyl acetate solution was washed with water, 5% NaHCO₃ solution, water and then dried over anhydrous sodium sulphate. Evaporation of the organic solution gave a mobile yellow oil. Column chromatography in ethyl acetate-petrol (1:1) gave a colourless oil (2.2 g). A solution of this oil (2.12 g) in methanol (125 ml) was treated with a solution of NaHCO₃ (0.964 g) in water (18.5 ml). The mixture was refluxed for 1 hr., then concentrated under vacuum. The residue was partitioned between ethyl acetate and water. The ethyl acetate solution was washed with water and dried over anhydrous sodium sulphate. Evaporation of the organic solution gave a white foam (1.541 g) which was crystallised from ether/petrol to give crystals (1.193 g). A portion (0.200 g) was recrystallised from ether/petrol to give white crystals of the title compound (0.126 g), m.p. 87°-99°, $[\alpha]_D$ +111.3°.

We claim:

1. Steroids of the pregnane and androstane series and their 19-nor analogues having a 3α-hydroxy group; a 5α-hydrogen atom or a 4,5- or 5,6-double bond; a 17α-hydrogen atom; and at the 11β-position a group of the formula $R^1COO-$ where $R^1$ is a $C_{1-6}$alkyl group or a monocyclic aralkyl group having a $C_{1-6}$alkyl portion, the alkyl group or alkyl portion being substituted by an amino group of the formula $-NR^aR^b$, in which $R^a$ and $R^b$, which may be the same or different, are hydrogen atoms, alkyl, alkenyl, cycloalkyl, cycloalkenyl or phenalkyl groups, provided that at least one of $R^a$ and $R^b$ is other than hydrogen and that $R^a$ and $R^b$ together contain up to 14 carbon atoms, or in which $R^a$ and $R^b$, together with the nitrogen atom, represent a saturated or ethylenically unsaturated non-aromatic monocyclic heterocyclic group having 3–10 ring members or a saturated or unsaturated bicyclic heterocyclic group having up to 10 ring carbon atoms, the ring containing the nitrogen atom being non-aromatic and either saturated or ethylenically unsaturated, which heterocyclic groups may be unsubstituted or substituted by $C_{1-4}$alkyl; the 17α-hydrogen D-homo analogues thereof; and the acid addition salts thereof.

2. Compounds as claimed in claim 1, which compounds are of the formula:

wherein:
$R^1$ is as defined in claim 1;
$R^2$ is a hydrogen atom or a methyl group;
$R^3$ is a hydrogen atom or optionally, when $R^4$ is a hydrogen atom, a $C_{1-3}$ alkyl group;
$R^4$ is a hydrogen atom or $C_{1-5}$ alkyl, $C_{1-5}$ alkoxy which may be substituted by a halogen atom or a phenyl group, $C_{2-5}$ alkanoyloxy, $C_{2-5}$ alkanoylthio, or thiocyanato group or a halogen atom;
$R^5$ is a hydrogen atom or a methyl group;
$R^6$ is a hydrogen atom or a methyl group;
$R^7$ represents two hydrogen atoms; a hydrogen atom in the β-position and a chlorine atom or methyl group in the α-position; a methyl group in the β-position and a hydrogen atom in the α-position; or a gem-dimethyl group; and
$R^8$ is a cyano group or a group —$COR^9$ where $R^9$ is a methyl group or a methyl group substituted by a fluorine atom, a $C_{1-4}$ alkoxy, hydroxy, methyl, chloromethyl, methoxymethyl, ethoxymethyl, $C_{2-5}$ alkanoyloxy, $C_{2-5}$ alkanoylthio, benzoyloxy, benzoylthio, or $C_{2-5}$ alkoxycarbonyloxy group; or where $R^9$ is a $C_{1-5}$ alkoxy, $C_{1-5}$ alkylthio or cyclopropyl group; or where $R^9$ is the group -$NR^xR^y$ where $R^x$ and $R^y$, which may be the same or different, are methyl or ethyl groups;
the broken lines indicate the optional presence of double bonds at the positions shown;
provided that $R^3$ and $R^4$ together represent a hydrogen atom when a 1,2-double bond is present; that the 2-position is saturated when a 4,5-double bond is present; and that the 6-position is saturated when a 8,9-double bond is present; and the D-homo analogues carrying $R^8$ at the 17aβ-position and $R^7$ at the 17-position;
and the acid addition salts thereof.

3. Compounds as claimed in claim 1 said compounds being 20-oxo pregnanes or 20-oxo D-homo pregnanes.

4. Compounds as claimed in claim 1 which possess a 5α-hydrogen atom and 10-methyl group, which possess no carbon-carbon double bonds in the tetracyclic steroid system and possess hydrogen atoms at the 2α, 3β, 6β and 16-positions, in which ring D is a 5-membered ring, and which possess a 17β-acetyl group or are 17β-cyano androstanes.

5. Compounds as claimed in claim 1 wherein $R^1$ is an N-mono-or N,N-disubstituted aminomethyl, aminoethyl aminopropyl, aminobutyl, amino-iso-butyl or aminobenzyl group.

6. Compounds as claimed in claim 5 wherein $R^1$ is an N-mono-or N,N-disubstituted aminomethyl or 1-aminoethyl group.

7. Compounds as claimed in claim 2 in which $R^1$ is an N-mono- or N,N-disubstituted aminomethyl or 1-aminoethyl group and wherein $R^a$ and $R^b$ are both unsubstituted alkyl groups, which may be the same or different, or one of $R^a$ and $R^b$ is a hydrogen atom and the other is an unsubstituted alkyl group.

8. Compounds as claimed in claim 7 wherein $R^a$ and $R^b$ together contain 4–9 carbon atoms.

9. Compounds as claimed in claim 8 wherein $R^a$ and $R^b$ are both ethyl or propyl groups, or wherein one of $R^a$ and $R^b$ is a methyl or ethyl group and the other contains 4–6 carbon atoms, or wherein one of $R^a$ and $R^b$ is a hydrogen atom and the other contains 5–7 carbon atoms.

10. Compounds as claimed in claim 2 in which $R^1$ is an N,N-disubstituted aminomethyl or 1-aminoethyl group and wherein —$NR^aR^b$ is a monocyclic heterocyclic group having 5–7 ring members, which may be unsubstituted or substituted by a methyl group.

11. Compounds as claimed in claim 10 wherein the heterocyclic group is a pyrrolidino, piperidino, hexamethylenimino or a 2-, 3- or 4-methylpiperidino group.

12. Compounds as claimed in claim 2 in which $R^1$ is an N-mono- or N,N-disubstituted aminomethyl or 1-aminomethyl group and wherein one of $R^a$ and $R^b$ is a hydrogen atom or a methyl or ethyl group, and the other is an allyl, cyclohexyl, cyclopentyl, cyclopropyl, benzyl or phenethyl group.

13. Compounds as claimed in claim 2 wherein $R^1$ is an N-mono- or N,N-disubstituted aminomethyl group.

14. Compounds as claimed in claim 2 which possess a 2β-hydrogen atom or $C_{1-5}$ alkoxy group.

15. Compounds as claimed in claim 1 in the form of their hydrochloride, hydrobromide, phosphate, sulphate, p-toluenesulphonate, methanesulphonate, citrate, tartrate, acetate, ascorbate, lactate, maleate, succinate, tricarballylate, glutarate, aconitate, citraconate or glutaconate salts.

16. Pharmaceutical compositions comprising a compound as claimed in claim 1, together with a pharmaceutical carrier or excipient.

17. A composition as claimed in claim 16 wherein said compound is in solution in a parenterally acceptable vehicle.

18. A composition as claimed in claim 17 in the form of a simple aqueous solution of a salt of said compound.

19. A process for the preparation of a compound as claimed in claim 1, which process comprises
reaction of an amine $HNR^aR^b$, where $R^a$ and $R^b$ are as defined in claim 1, with a corresponding 11β-alkanoyloxy or 11β-aralkanoyloxy compound having a readily displaceable substituent in the alkyl portion.

20. 11β-Halo esters of the pregnane and androstane series and their 19-nor and D-homo analogues having the structure as defined in claim 1 wherein $R^1$ is a $C_{1-6}$ alkyl group or a monocyclic aralkyl group having a C$_{1-6}$ alkyl portion, the alkyl group or portion being substituted by a halogen atom.

21. A compound as claimed in claim 1, wherein said compound is 11β-N,N-dipropylaminoacetoxy-3α-hydroxy-5α-pregnan-20-one, 11β-N,N-dipropylaminoacetoxy-3α-hydroxy-5α-pregnan-20-one phosphate, 11β-N,N-dipropylaminoacetoxy-3α-hydroxy-5α-pregnan-20-one citrate, 11β-N,N-dipropylaminoacetoxy-3α-hydroxy-5α-pregnan-20-one tricarballylate, 11β-N,N-dipropylaminoacetoxy-3α-hydroxy-5α-pregnan-20-one hydrochloride, 11β-N,N-dipropylaminoacetoxy-3α-hydroxy-5α-pregnan-20-one hemisulphate, 11β-dipropylaminoacetoxy-3α-hydroxy-5α-pregnan-20-one tartrate, 11β-N,N-dipropylaminoacetoxy-3α-hydroxy-5α-pregnan-20-one lactate and 11β-N,N-dipropylaminoacetoxy-3α-hydroxy-5α-pregnan-20-one glutarate, 11β-piperidinoacetoxy-3α-hydroxy-5α-pregnan-20-one, 11β-piperidinoacetoxy-3α-hydroxy-5α-pregnan-20-one citrate, 11β-piperidinoacetoxy-3α-hydroxy-5α-pregnan-20-one hydrochloride, 11β-(3-methylpiperidinoacetoxy)-3α-hydroxy-5α-pregnan-20-one, 11β-(3-methylpiperidinoacetoxy)-3α-hydroxy-5α-pregnan-20-one citrate, 11β-(4-methylpiperidinoacetoxy)-3α-hydroxy-5α-pregnan-20-one, 11β-(4-methylpiperidinoacetoxy)-3α-hydroxy-5α-pregnan-20-one citrate, 11β-(2-methylpiperidinoacetoxy)-3α-hydroxy-5α-pregnan-20-one, 11β-(2-methylpiperidinoacetoxy)-3α-hydroxy-5α-pregnan-20-one citrate, 11β-hexamethyleniminoacetoxy-3α-hydroxy-5α-pregnan-20-one, 11β-hexamethyleniminoacetoxy-3α-hydroxy-5α-pregnan-20-one citrate; 2β-ethoxy-11β-N,N-dipropylaminoacetoxy-3α-hydroxy-5α-pregnan-20-one, 2β-ethoxy-11β-N,N-dipropylaminoacetoxy-3α-hydroxy-5α-pregnan-20-one citrate, 2β-ethoxy-11β-N,N-dipropylaminoacetoxy-3α-hydroxy-5α-pregnan-20-one tricarballylate, 2β-methyl-11β-N,N-dipropylaminoacetoxy-3α-hydroxy-5α-pregnan-20-one, 2β-methyl-11β-N,N-dipropylaminoacetoxy-3α-hydroxy-5α-pregnan-20-one citrate, 2β-ethoxy-11β-N-methyl-N-butylaminoacetoxy-3α-hydroxy-5α-pregnan-20-one, 2β-ethoxy-11β-N-methyl-N-butylaminoacetoxy-3α-hydroxy-5α-pregnan-20-one citrate, 2β-propoxy-11β-N,N-diethylaminoacetoxy-3α-hydroxy-5α-pregnan-20-one, 2β-propoxy-11β-N,N-diethylaminoacetoxy-3α-hydroxy-5α-pregnan-20-one citrate; 3α-hydroxy-3β-methyl-11β-piperidinoacetoxy-5α-pregnan-20-one, 3α-hydroxy-3β-methyl-11β-piperidinoacetoxy-5α-pregnan-20-one citrate; 17β-cyano-3α-hydroxy-11β-N,N-dipropylaminoacetoxy-5α-androstane, 17β-cyano-3α-hydroxy-11β-N,N-dipropylaminoacetoxy-5α-androstane citrate; 3α-hydroxy-11β-N-methyl-N-1',3'-dimethylbutylaminoacetoxy-5α-pregnan-20-one, 3α-hydroxy-11β-N-methyl-N-1',3'-dimethylbutylaminoacetoxy-5α-pregnan-20-one citrate; 11β-N,N-diethylaminoacetoxy-3α-hydroxy-5α-pregnan-20-one, 11β-N,N-diethylaminoacetoxy-3α-hydroxy-5α-pregnan-20-one citrate; 2β-bromo-3α-hydroxy-11β-N-butyl-N-methylaminoacetoxy-5α-pregnan-20-one, 2β-bromo-3α-hydroxy-11β-N-butyl-N-methylaminoacetoxy-5α-pregnan-20-one citrate; 11β-N-butyl-N-methylaminoacetoxy-17β-cyano-3α-hydroxy-5α-androstane or 11β-N-butyl-N-methylaminoacetoxy-17β-cyano-3α-hydroxy-5α-androstane citrate.

22. A compound as claimed in claim 1, which is 11β-N,N diethylaminoacetoxy-2β-ethoxy-3α-hydroxy-5α-pregnan-20-one, 11β-N,N-diethylaminoacetoxy-2β-ethoxy-3α-hydroxy-5α-pregnan-20-one citrate; 11β-N-methyl-N-butylaminoacetoxy-3α-hydroxy-5α-pregnan-20-one, 11β-N-methyl-N-butylaminoacetoxy-3α-hydroxy-5α-pregnan-20-one citrate; 11β-N-ethyl-N-butylaminoacetoxy-3α-hydroxy-5α-pregnan-20-one, 11β-N-ethyl-N-butylaminoacetoxy-3α-hydroxy-5α-pregnan-20-one citrate, 11β-N-ethyl-N-butylaminoacetoxy-3α-hydroxy-5α-pregnan-20-one hydrochloride or 11β-N-ethyl-N-butylaminoacetoxy-3α-hydroxy-5α-pregnan-20-one tricarballylate.

23. A compound as claimed in claim 1, said compound being: 3α-hydroxy-11β-N-2'-methylbutylaminoacetoxy-5α-pregnan-20-one, 3α-hydroxy-11β-N-2'-methylbutylaminoacetoxy-5α-pregnan-20-one citrate; 3α-hydroxy-11β-N-methyl-N-2'-methylbutylaminoacetoxy-5α-pregnan-20-one, 3α-hydroxy-11β-N-methyl-N-2'-methylbutylaminoacetoxy-5α-pregnan-20-one citrate; 3α-hydroxy-11β-N-methyl-N-[(2R)-1',3'dimethylbutyl]aminoacetoxy-5α-pregnan-20-one, 3α-hydroxy-11β-N-methyl-N-[(2R)-1',3'-dimethylbutyl]aminoacetoxy-5α-pregnan-20-one citrate; 3α-hydroxy-11β-N-methyl-N-[(2S)-1',3'-dimethylbutyl]aminoacetoxy-5α-pregnan-20-one, 3α-hydroxy-11β-N-methyl-N-[(2S)-1',3'-dimethylbutyl]aminoacetoxy-5α-pregnan-20-one citrate; 11β-N,N-di(but-2-yl)aminoacetoxy-3α-hydroxy-5α-pregnan-20-one, 11β-N,N-di(but-2-yl)aminoacetoxy-3α-hydroxy-5α-pregnan-20-one citrate; 11β-N-1',3'-dimethylbutyl-N-ethylaminoacetoxy-3α-hydroxy-5α-pregnan-20-one, 11β-N-1',3'-dimethylbutyl-N-ethylaminoacetoxy-3α-hydroxy-5α-pregnan-20-one citrate; 11β-N-2',2'-dimethylpropylaminoacetoxy-3α-hydroxy-5α-pregnan-20-one, 11β-N-2'2'-dimethylpropylaminoacetoxy-3α-hydroxy-5α-pregnan-20-one citrate; 11β-N,N-diethylaminoacetoxy-3α-hydroxy-2β-methyl-5α-pregnan-20-one, 11β-N,N-diethylaminoacetoxy-3α-hydroxy-2β-methyl-5α-pregnan-20-one citrate; 11β-N-ethyl-N-butylaminoacetoxy-3α-hydroxy-2β-methyl-5α-pregnan-20-one, 11β-N-ethyl-N-butylaminoacetoxy-3α-hydroxy-2β-methyl-5α-pregnan-20-one citrate; 3α-hydroxy-2β-methyl-11β-(4'-methylpiperidinoacetoxy)-5α-pregnan-20-one, 3α-hydroxy-2β-methyl-11β-(4'methylpiperidinoacetoxy)-5α-pregnan-20-one citrate; 2β-ethoxy-3α-hydroxy-11β-N-3'-methylbutylaminoacetoxy-5α-pregnan-20-one, 2β-ethoxy-3α-hydroxy-11β-N-3'-methylbutylaminoacetoxy-5α-pregnan-20-one citrate; 2β-ethoxy-3α-hydroxy-11β-N-1',3'-dimethylbutylaminoacetoxy-5α-pregnan-20-one, 2β-ethoxy-3α-hydroxy-11β-N-1',3'-dimethylbutylaminoacetoxy-5α-pregnan-20-one citrate; 11β-N,N-diethylaminoacetoxy-3α-hydroxy-2β-iso-propoxy-5α-pregnan-20-one, or 11β-N,N-diethylaminoacetoxy-3α-hydroxy-2β-iso-propoxy-5α-pregnan-20-one citrate.

* * * * *